US012433583B1

(12) United States Patent
Amin

(10) Patent No.: US 12,433,583 B1
(45) Date of Patent: Oct. 7, 2025

(54) SUTURE PASSER DEVICES, SYSTEMS, AND METHODS

(71) Applicant: Integrity Medical Services Inc., Yorba Linda, CA (US)

(72) Inventor: Nirav H. Amin, Yorba Linda, CA (US)

(73) Assignee: Integrity Medical Services Inc., Yorba Linda, CA (US)

( * ) Notice: Subject to any disclaimer, the term of this patent is extended or adjusted under 35 U.S.C. 154(b) by 0 days.

(21) Appl. No.: 19/224,346

(22) Filed: May 30, 2025

Related U.S. Application Data

(60) Provisional application No. 63/654,779, filed on May 31, 2024.

(51) Int. Cl.
*A61B 17/04* (2006.01)
*A61B 17/062* (2006.01)
*A61B 17/06* (2006.01)

(52) U.S. Cl.
CPC ...... *A61B 17/0491* (2013.01); *A61B 17/0483* (2013.01); *A61B 17/0485* (2013.01); *A61B 17/062* (2013.01); *A61B 2017/047* (2013.01); *A61B 2017/0608* (2013.01)

(58) Field of Classification Search
CPC ............ A61B 17/0491; A61B 17/0483; A61B 17/0485; A61B 17/062; A61B 2017/047; A61B 2017/0608
See application file for complete search history.

(56) References Cited

U.S. PATENT DOCUMENTS

| | | | |
|---|---|---|---|
| 4,922,897 | A | 5/1990 | Sapega et al. |
| 5,112,337 | A | 5/1992 | Paulos et al. |
| 5,154,720 | A | 10/1992 | Trott et al. |
| 5,163,940 | A | 11/1992 | Bourque |
| 5,201,741 | A | 4/1993 | Dulebohn |
| 5,330,468 | A | 7/1994 | Burkhart |
| 5,374,269 | A | 12/1994 | Rosenberg |
| 5,417,684 | A | 5/1995 | Jackson et al. |
| 5,501,692 | A | 3/1996 | Riza |
| 5,709,697 | A | 1/1998 | Ratcliff et al. |

(Continued)

FOREIGN PATENT DOCUMENTS

| | | |
|---|---|---|
| CN | 104083204 | 6/2016 |
| CN | 208081271 | 11/2018 |

(Continued)

OTHER PUBLICATIONS

Anika Sports Medicine, ProPass™ Suture Passer, AML-900-521 Sell Sheet; 2023, downloaded on Jun. 5, 2025 from URL: https://anika.com/wp-content/uploads/2024/04/AML-900-521_ProPass-Sell-Sheet.pdf; 1 page.

(Continued)

*Primary Examiner* — Phong Son H Dang
(74) *Attorney, Agent, or Firm* — Knobbe Martens Olson & Bear, LLP

(57) ABSTRACT

A suture passer for passing a suture across a tissue. The suture passer can include an upper jaw member and a lower jaw member extending from an elongate member. The lower jaw member can have a curved portion that offsets a straight portion of the lower jaw member from the central axis of the elongate member. The lower jaw member can house a needle that can be deployed across a tissue to pass a suture across.

20 Claims, 33 Drawing Sheets

(56) References Cited

U.S. PATENT DOCUMENTS

| | | | | |
|---|---|---|---|---|
| 5,810,828 | A | 9/1998 | Lightman et al. | |
| 5,817,111 | A | 10/1998 | Riza | |
| 5,865,834 | A | 2/1999 | McGuire | |
| 5,895,389 | A | 4/1999 | Schenk | |
| 5,980,538 | A * | 11/1999 | Fuchs ................ | A61B 17/0469 606/139 |
| 5,993,451 | A | 11/1999 | Burkhart | |
| 6,022,360 | A | 2/2000 | Reimels et al. | |
| 6,063,088 | A | 5/2000 | Winslow | |
| 6,120,511 | A | 9/2000 | Chan | |
| 6,254,605 | B1 | 7/2001 | Howell | |
| 6,676,668 | B2 | 1/2004 | Mercereau et al. | |
| 7,192,431 | B2 | 3/2007 | Hangody et al. | |
| 7,210,881 | B2 | 5/2007 | Greenberg | |
| 7,270,663 | B2 | 9/2007 | Nakao | |
| 7,575,578 | B2 | 8/2009 | Wetzler et al. | |
| 7,578,824 | B2 | 8/2009 | Justin et al. | |
| 7,585,305 | B2 | 9/2009 | Dreyfuss | |
| 7,771,483 | B2 | 8/2010 | Justin et al. | |
| 7,972,344 | B2 | 7/2011 | Murray et al. | |
| 8,177,796 | B2 | 5/2012 | Akyuz et al. | |
| 8,282,656 | B2 | 10/2012 | Hart | |
| 8,523,872 | B2 | 9/2013 | Ek | |
| 8,690,885 | B2 | 4/2014 | Smith | |
| 8,740,913 | B2 | 6/2014 | Schneider | |
| 8,888,795 | B2 | 11/2014 | Chu | |
| 9,023,056 | B2 | 5/2015 | Berberich | |
| 9,161,764 | B2 | 10/2015 | Smith | |
| 9,232,954 | B2 | 1/2016 | Steiner et al. | |
| 9,451,951 | B2 | 9/2016 | Sullivan et al. | |
| 9,668,726 | B1 * | 6/2017 | Bourland, III ..... | A61B 17/0482 |
| 9,687,225 | B2 * | 6/2017 | Palese ................ | A61B 17/0401 |
| 9,848,868 | B2 * | 12/2017 | Saliman ............. | A61B 17/0625 |
| 9,877,732 | B2 * | 1/2018 | Raybin .............. | A61B 17/1227 |
| 10,098,646 | B2 | 10/2018 | Ardito et al. | |
| 10,278,689 | B2 | 5/2019 | Palese et al. | |
| 10,492,804 | B2 | 12/2019 | Amis et al. | |
| 10,524,778 | B2 | 1/2020 | Hendricksen et al. | |
| 10,758,251 | B2 | 9/2020 | Miller | |
| 10,765,422 | B2 * | 9/2020 | Heneveld ........... | A61B 17/0469 |
| 10,799,334 | B2 | 10/2020 | Smigielski et al. | |
| 10,888,349 | B2 | 1/2021 | Pereira et al. | |
| 10,905,412 | B2 | 2/2021 | Hirotsuka et al. | |
| 10,973,511 | B2 | 4/2021 | Topper et al. | |
| 11,033,283 | B2 | 6/2021 | Mirochinik et al. | |
| 11,166,732 | B2 | 11/2021 | Maxon et al. | |
| 11,202,641 | B2 | 12/2021 | Biton et al. | |
| 11,357,517 | B1 | 6/2022 | Amin | |
| 11,471,150 | B2 | 10/2022 | Smith et al. | |
| 11,504,140 | B2 | 11/2022 | Fallin et al. | |
| 11,723,651 | B1 * | 8/2023 | Simon ................ | A61B 17/0218 606/144 |
| 11,903,602 | B2 | 2/2024 | Sullivan et al. | |
| 11,918,203 | B2 | 3/2024 | Murillo et al. | |
| 11,986,193 | B2 | 5/2024 | Amin | |
| 12,023,049 | B2 | 7/2024 | Amin | |
| 12,029,412 | B2 | 7/2024 | Heneveld | |
| 12,102,338 | B2 | 10/2024 | Amin | |
| 12,274,454 | B2 | 4/2025 | Amin | |
| 12,285,181 | B2 | 4/2025 | Amin | |
| 2002/0133165 | A1 | 9/2002 | Whittaker et al. | |
| 2004/0176771 | A1 | 9/2004 | Schmieding | |
| 2004/0249394 | A1 * | 12/2004 | Morris ............... | A61B 17/0625 606/222 |
| 2005/0203523 | A1 | 9/2005 | Wenstrom et al. | |
| 2005/0288690 | A1 * | 12/2005 | Bourque ............ | A61B 17/0469 606/144 |
| 2006/0173468 | A1 | 8/2006 | Simmon et al. | |
| 2006/0293689 | A1 | 12/2006 | Miller et al. | |
| 2007/0233128 | A1 | 10/2007 | Schmieding | |
| 2008/0154271 | A1 | 6/2008 | Berberich et al. | |
| 2008/0183174 | A1 | 7/2008 | Sikora et al. | |
| 2008/0208221 | A1 * | 8/2008 | Murray .............. | A61B 17/0625 606/145 |
| 2009/0171359 | A1 | 7/2009 | Sterrett | |
| 2011/0125156 | A1 | 5/2011 | Sharkey | |
| 2011/0130773 | A1 * | 6/2011 | Saliman ............. | A61B 17/0469 606/145 |
| 2011/0166581 | A1 | 7/2011 | Van Der Merwe et al. | |
| 2011/0238074 | A1 | 9/2011 | Ek | |
| 2011/0270280 | A1 * | 11/2011 | Saliman ............. | A61B 17/0469 606/145 |
| 2012/0109136 | A1 | 5/2012 | Bourque et al. | |
| 2012/0283754 | A1 * | 11/2012 | Murillo .............. | A61B 17/0469 606/145 |
| 2014/0155899 | A1 | 6/2014 | Bowman et al. | |
| 2014/0276844 | A1 | 9/2014 | Bourque et al. | |
| 2014/0276884 | A1 | 9/2014 | Lizardi et al. | |
| 2015/0066040 | A1 | 3/2015 | Harbison et al. | |
| 2015/0133941 | A1 | 5/2015 | Saylor et al. | |
| 2015/0190147 | A1 | 7/2015 | Ferragamo et al. | |
| 2015/0345927 | A1 | 12/2015 | Bourque et al. | |
| 2015/0351777 | A1 | 12/2015 | Lizardi et al. | |
| 2016/0089161 | A1 | 3/2016 | Ardito et al. | |
| 2017/0007279 | A1 | 1/2017 | Sharma | |
| 2017/0042556 | A1 | 2/2017 | LaPrade et al. | |
| 2017/0172565 | A1 * | 6/2017 | Heneveld ......... | A61B 17/06004 |
| 2017/0189036 | A1 | 7/2017 | Rajeev | |
| 2017/0245869 | A1 | 8/2017 | Mirochinik | |
| 2018/0153572 | A1 | 6/2018 | Fojtik et al. | |
| 2020/0275922 | A1 | 9/2020 | Valentin et al. | |
| 2020/0375615 | A1 | 12/2020 | Walker | |
| 2022/0110640 | A1 | 4/2022 | Kam et al. | |
| 2022/0117720 | A1 | 4/2022 | Ng et al. | |
| 2022/0249087 | A1 | 8/2022 | Diduch et al. | |
| 2022/0296083 | A1 | 9/2022 | Wilson et al. | |
| 2023/0135885 | A1 | 5/2023 | Snyder et al. | |
| 2023/0157808 | A1 | 5/2023 | Cole et al. | |
| 2024/0032911 | A1 | 2/2024 | Murillo et al. | |
| 2025/0017719 | A1 | 1/2025 | Amin | |

FOREIGN PATENT DOCUMENTS

| | | |
|---|---|---|
| CN | 217853139 U | 11/2022 |
| EP | 2419035 | 7/2017 |
| WO | WO 2018/075615 | 4/2018 |

OTHER PUBLICATIONS

Arthrex, FiberSnare® Suture. Undated; downloaded Jul. 17, 2024 from https://www.arthrex.com/knee/fibersnare; 4 pages.

DAIC—Diagnostic and Interventional Cardiology, SentreHeart Receives CE Mark for Lariat Suture Delivery Device. News Article; Oct. 28, 2015; downloaded from https://www.dicardiology.com/content/sentreheart-receives-ce-mark-lariat-suture-delivery-device; 1 page.

Espejo-Baena et al., Posterior Cruciate Ligament Reconstruction With Hamstring Tendons Using a Suspensory Device for Tibial Fixation and Interference Screw for Femoral Fixation. Arthroscopy Techniques. Feb. 1, 2017;6(1): e213-e218.

OuYang et al., A Modfied Mason-Allen Suture Enhancement Technique (Sunglasses Loop) for Single-row Repair of Medium-to-large Rotator Cuffs. Arthros Tech. Jul. 1, 2024;13(7):103007 in 8 pages.

Petry A., SutureSnare™ Suture Passer—Product Demonstration; Anthrex Apr. 25, 2016, downloaded from https://www.arthrex.com/resources/VID1-00773-EN/suturesnare-suture-passer on Jul. 17, 2024; 4 pages.

Steris Healthcare, Lariat® Snare. Product Details, undated, downloaded from https://www.steris.com/healthcare/products/endoscopy-devices/polypectomy-and-tissue-acquisition-devices/lariat-snare; 4 pages.

Stryker, Champion Suture Passer, 1998-2025, downloaded on Jun. 5, 2025 from URL: https://www.stryker.com/us/en/sports-medicine/products/champion-suture-passer.html; 4 pages.

Yin et al., Transtibial Pull-Out Repair of Converted Radial Tear Adjacent to Medial Meniscus Root. Arthroscopy Techniques.Jan. 1, 2020;9(1): e171-e176.

Zimmer Biomet, SpeedSnare™ Surgical Suture Passer. Website for Healthcare Professionals; undated downloaded on Jul. 17, 2024

(56) References Cited

OTHER PUBLICATIONS from https://www.zimmerbiomet.com/en/products-and-solutions/specialties/sports-medicine/speedsnare-surgical-suture-passer.html, 8 pages.

* cited by examiner

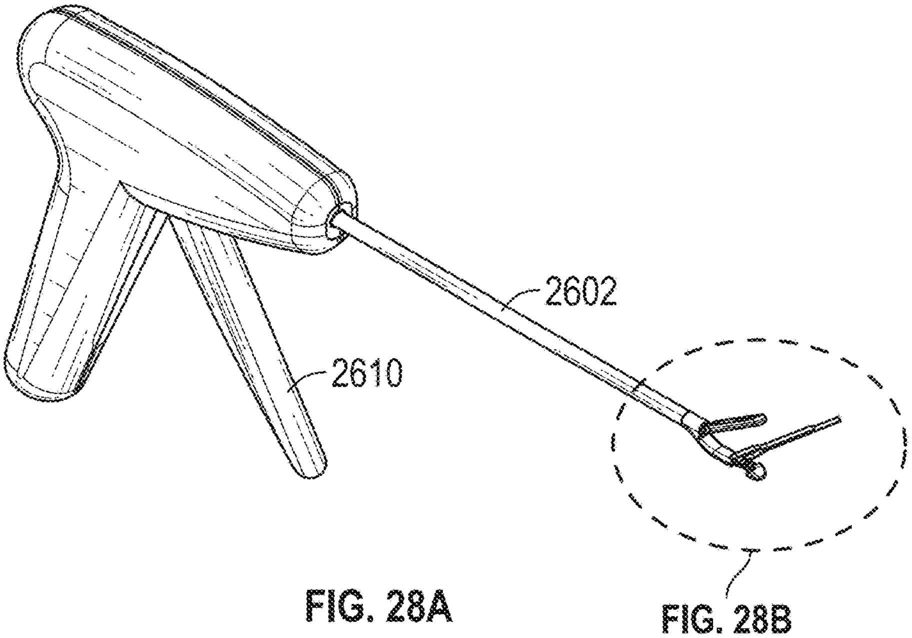
FIG. 28A
FIG. 28B
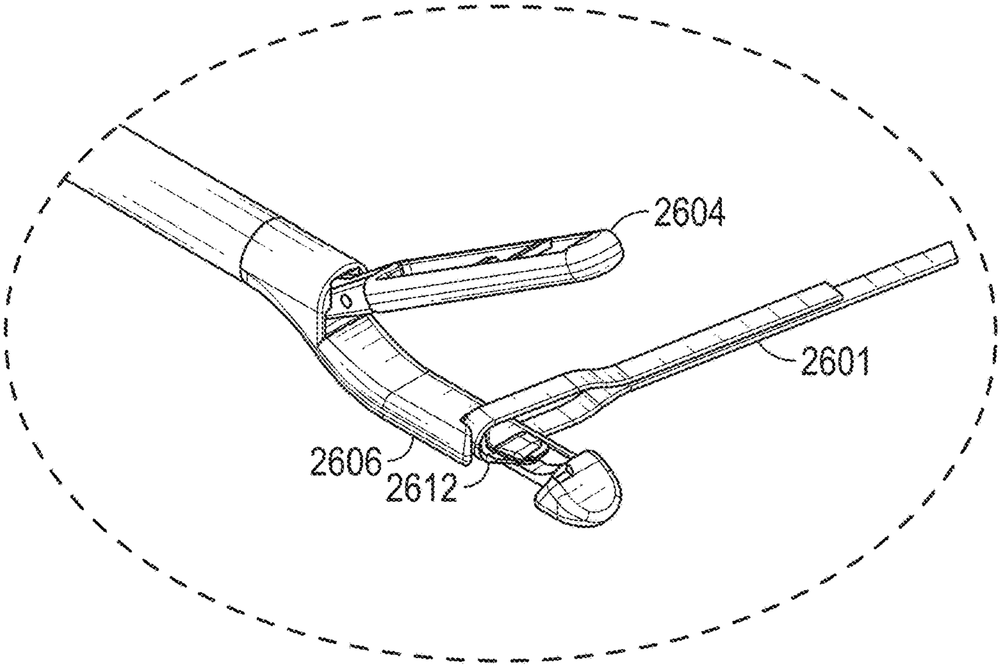
FIG. 28B
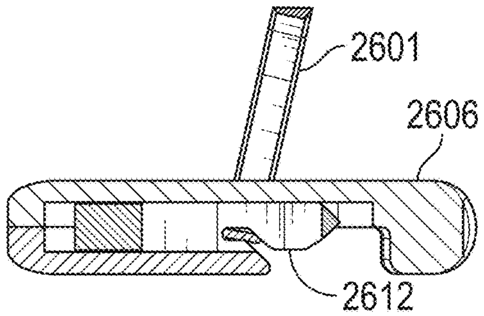
FIG. 28C

SUTURE PASSER DEVICES, SYSTEMS, AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated in their entireties by reference under 37 CFR 1.57. In particular, this application claims priority to the U.S. Provisional Application 63/654,779, filed May 31, 2024, which is incorporated by reference herein in its entirety.

TECHNICAL FIELD

The present disclosure relates to the field of surgical methods and devices, and more particularly to systems, methods, and devices for suturing tissue in difficult to access regions.

BACKGROUND

Suturing tissue during surgical procedures can be difficult in certain regions of the body. Suture passers can assist with repairing tissue by passing a suture from one side of the tissue to the other. Suture passers can be used for orthopedic surgeries, general surgeries, cardiovascular surgeries, gynecological surgeries, urological surgeries, neurosurgeries, and reconstructive surgeries.

Suture passers in the field can pass a suture from a lower jaw to an upper jaw, across a tissue. However, current suture passers have difficulty with soft tissue, which can be damaged when engaged by the jaws. Additionally, the needle that passes from the lower jaw to the upper jaw can be difficult to manage once deployed, causing a risk of damage to surrounding tissue. To load the suture into the suture passer, the suture typically must be tied, threaded, or fed through one of the jaw members or the needle before using the device. The suture must be unloaded by untying the suture from the device or removing it from the needle.

SUMMARY

The suture passers described herein can have a curved lower jaw, allowing the suture passer to engage tissue with a lower risk of tissue damage. Particularly, the curved lower jaw can more easily maneuver under soft tissue without causing damage. The needle that passes the suture from the lower jaw through the upper jaw can curve downward once deployed. The downward curvature of the needle can be caused by the force, velocity, and/or momentum undergone during deployment. The downward slope of the needle can make it easier to manage and reduce the risk of damaging surrounding tissue.

In some examples, the systems described herein can include: a handle including a trigger; an elongate member extending from the handle; a first jaw member extending from a distal end of the elongate member and configured for angular movement relative to the elongate member; and a second jaw member extending from the distal end of the elongate member, the second jaw member including: a curved portion extending from the distal end of the elongate member and curved away from the first jaw member; a straight portion extending from a distal end of the curved portion; and a tissue penetrator positioned on the straight portion of the second jaw member, the tissue penetrator configured to shift between a retracted position and an engaged position, the tissue penetrator configured to be parallel with the straight portion of the second jaw member in the retracted position, and the tissue penetrator configured to extend through the first jaw member in the engaged position, wherein the trigger is configured to shift the tissue penetrator between the retracted position and the engaged position.

In some examples, the tissue penetrator is a needle. In some examples, a distal end of the needle is curved toward the second jaw member in the engaged position. In some examples, the second jaw member includes a shoulder configured to direct the tissue penetrator toward the first jaw member. In some examples, the system can include a suture loader in the second jaw member. In some examples, the suture loader includes a notch in the straight portion of the second jaw member. In some examples, the suture loader includes a slot perpendicular to the notch and aligned with the tissue penetrator. In some examples, the system can include a notch in the tissue penetrator and a suture retainer, wherein a notch of the tissue penetrator is configured to capture a suture loop, the tissue penetrator is configured to move the suture loop through the first jaw member, and the suture retainer is configured to retain the suture loop. In some examples, the system can include the suture loop, the suture loop configured to be released from the suture retainer by pulling on an end of the suture loop. In some examples, the notch of the tissue penetrator is proximal to a distal end of the tissue penetrator.

In some examples, the devices described herein can include: an elongate member configured to be coupled with a handle including a trigger; a first jaw member extending from a distal end of the elongate member and configured for angular movement relative to the elongate member; and a second jaw member extending from the distal end of the elongate member, the second jaw member including: a curved portion extending from the distal end of the elongate member and curved away from the first jaw member; a straight portion extending from a distal end of the curved portion; and a tissue penetrator positioned on the straight portion of the second jaw member, the tissue penetrator configured to shift between a retracted position and an engaged position, the tissue penetrator configured to be parallel with the straight portion of the second jaw member in the retracted position, and the tissue penetrator configured to extend through the first jaw member in the engaged position, wherein the tissue penetrator is configured to shift between the retracted position and the engaged position by actuating the trigger when the handle and the elongate member are coupled.

In some examples, the tissue penetrator is a needle. In some examples, a distal end of the needle is curved toward the second jaw member in the engaged position. In some examples, the second jaw member includes a shoulder configured to direct the tissue penetrator toward the first jaw member. In some examples, the device can include a suture loader in the second jaw member. In some examples, the suture loader includes a notch in the straight portion of the second jaw member. In some examples, the suture loader includes a slot perpendicular to the notch and aligned with the tissue penetrator. In some examples, the device can include a notch in the tissue penetrator and a suture retainer, wherein a notch of the tissue penetrator is configured to capture a suture loop, the tissue penetrator is configured to move the suture loop through the first jaw member, and the suture retainer is configured to retain the suture loop. In some examples, the device can include the suture loop, the suture loop configured to be released from the suture retainer by pulling on an end of the suture loop.

In some examples, the methods described herein can include: providing a suture passer including: an elongate member; a first jaw member extending from a distal end of the elongate member; and a second jaw member extending from the distal end of the elongate member, the second jaw member including: a curved portion extending from the distal end of the elongate member and curved away from the first jaw member; a straight portion extending from a distal end of the curved portion; and positioning a suture through the second jaw member such that the suture engages a tissue penetrator; positioning the first jaw member and the second jaw member around a tissue; moving the first jaw member toward the second jaw member to engage the tissue; and deploying the tissue penetrator from the second jaw member through the tissue and through the first jaw member.

In some examples, the method can include retracting the tissue penetrator in the second jaw member. In some examples, the method can include moving the first jaw member away from the second jaw member. In some examples, deploying the tissue penetrator includes abutting, with the tissue penetrator, a shoulder of the second jaw member. In some examples, moving the first jaw member toward the second jaw member includes actuating a trigger to move the first jaw member toward the second jaw member. In some examples, deploying the tissue penetrator from the second jaw member includes actuating a trigger to deploy the tissue penetrator from the second jaw member. In some examples, positioning the suture includes positioning the suture in a notch in the tissue penetrator such that the tissue penetrator is configured to move a suture loop through the first jaw member. In some examples, deploying the tissue penetrator includes capturing the suture in a suture retainer, the suture retainer configured to retain a suture loop. In some examples, the suture loop is configured to be released from the suture retainer by pulling on an end of the suture loop. In some examples, the notch of the tissue penetrator is proximal to a distal end of the tissue penetrator.

In some examples, the methods described herein can include: positioning a suture loop of a suture at least partially around a suture passer, the suture passer including: an elongate member; a first jaw member extending from a distal end of the elongate member; and a second jaw member extending from the distal end of the elongate member, the second jaw member including: a curved portion extending from the distal end of the elongate member and curved away from the first jaw member; a straight portion extending from a distal end of the curved portion; and positioning the first jaw member and the second jaw member around a tissue; moving the first jaw member toward the second jaw member to engage the tissue; and deploying a tissue penetrator from the second jaw member through the tissue and through the first jaw member such that the tissue penetrator captures the suture loop and pulls the suture at least partially through the tissue.

In some examples, the method can include retracting the tissue penetrator in the second jaw member. In some examples, the method can include moving the first jaw member away from the second jaw member. In some examples, deploying the tissue penetrator includes abutting, with the tissue penetrator, a shoulder of the second jaw member. In some examples, moving the first jaw member toward the second jaw member includes actuating a trigger to move the first jaw member toward the second jaw member. In some examples, deploying the tissue penetrator from the second jaw member includes actuating a trigger to deploy the tissue penetrator from the second jaw member. In some examples, positioning the suture includes positioning the suture loop in a notch in the tissue penetrator such that the tissue penetrator is configured to move the suture loop through the first jaw member. In some examples, deploying the tissue penetrator includes capturing the suture in a suture retainer, the suture retainer configured to retain a suture loop. In some examples, the suture loop is configured to be released from the suture retainer by pulling on an end of the suture loop. In some examples, the notch of the tissue penetrator is proximal to a distal end of the tissue penetrator.

BRIEF DESCRIPTION OF THE DRAWINGS

FIGS. 28A-28C show a suture positioned within a notch of a needle which can allow the needle to capture the suture.

DETAILED DESCRIPTION

Embodiments disclosed herein relate to devices, systems, and methods of suture passers. Some embodiments of devices disclosed herein relate to a device for passing a suture across soft tissue with reduced risk of tissue damage. Some embodiments disclosed herein relate to kits for use in suture passing. Some embodiments disclosed herein relate to methods of passing sutures across tissue.

The suture passer can be used to pass a suture from one side of a tissue to the other. For example, the suture passer can be used in a meniscal repair, a labral repair, an achilles tendon repair, a bankart repair, a biceps tenodesis, a subscapularis repair, or a latarjet procedure. Advantageously, this suture passer can be used to suture soft tissue with a reduced risk of tissue damage. Because soft tissue can vary in thickness and density, it can be difficult to penetrate and navigate through the tissue layers. Additionally, tissue trauma such as tearing, crushing, or perforation of the tissue can be more likely when suturing soft tissue. This can lead to impaired healing, increased scarring, or compromised tissue integrity. The structure of the jaws of the suture passer described herein can improve maneuverability and safety of the suture passer. Additionally, the configuration of the needle, or tissue penetrator, can improve the functionality of the suture passer. Additionally, the configuration of the suture passer can improve the method of loading and unloading the suture.

Figure 1A:
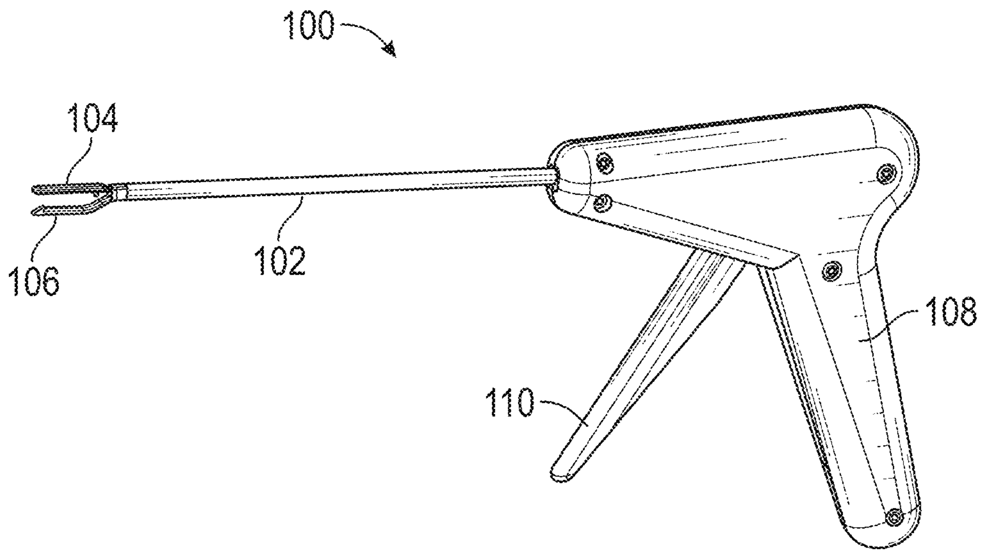
FIG. 1A shows an example of a suture passer.

FIG. 1A shows an example of a suture passer 100. In certain examples, the suture passer 100 can include a handle 108 for a user to hold the suture passer 100. An elongate member 102 can extend from the handle 108. At a distal end of the elongate member 102, which can also be referred to as a distal end of the suture passer 100, the suture passer 100 can include an upper jaw member 104 and a lower jaw member 106. The upper jaw member 104 can be a first jaw member. The lower jaw member 106 can be a second jaw member. At least one of the jaw members 104, 106 can move with respect to one another.

The suture passer 100 can include a trigger 110, for example on the handle 108. The trigger 110 can control movement of the jaw members 104, 106. The trigger 110 can control deployment of the tissue penetrator (which can be needle 112). The trigger 110 can shift the suture passer 100 between the open jaws configuration and the closed jaws configuration. The trigger 110 can shift the suture passer 100 between the needle undeployed and the needle deployed configuration. An open jaws configuration can be when the jaw members 104, 106 are pivoted away from each other such that the jaw members 104, 106 can be positioned over or around tissue, and a closed jaws configuration can be when one or both of the jaw members 104, 106 are pivoted towards each other such that the jaw members 104, 106 can clamp onto a tissue or become closer to the tissue. A needle undeployed configuration can be when a tissue penetrator (e.g., needle 112) is positioned partially or fully within one of the jaw members 104, 106, which can allow the jaw members 104, 106 to be positioned over or around tissue. A needle deployed configuration can be when the tissue penetrator (e.g., needle) is extended from the lower jaw member 106 or upper jaw member 104 such that the tissue penetrator can penetrate tissue positioned between the jaw members 104, 106.

In some embodiments, partially actuating the trigger 110 can cause the suture passer 100 to shift from the open jaws configuration to the closed jaws configuration. Partially actuating the trigger 110 can include moving the trigger partially (e.g., half-way towards a hand grip of the handle 108, or in a range from one-quarter to three-quarters of the way, or any value, approximate value, or range of values in the foregoing range). In some embodiments, partially actuating the trigger 110 can cause the upper jaw member 104 to pivot toward the lower jaw member 106. Partially actuating the trigger 110 can cause the lower jaw member 106 to pivot toward the upper jaw member 104. In some embodiments, fully actuating the trigger 110 can cause the suture passer 100 to shift from the needle undeployed to the needle deployed configuration. Fully actuating the trigger 110 can include moving the trigger all the way or nearly all the way towards a hand grip of the handle 108 (e.g., more than three-quarters of the way, or more than halfway, etc.) Fully actuating the trigger 110 can include moving the trigger from a partially actuated configuration all the way or nearly all the way towards a grip of the handle 108. Accordingly, fully actuating the trigger 110 can include moving the trigger from its starting position to the hand grip 108 and can include moving the trigger from a partially actuated configuration (e.g., half-way point) to the hand grip 108. In some embodiments, fully actuating the trigger 110 can cause the needle to deploy from the lower jaw member 106. In some embodiments, actuating a first trigger can cause the suture passer 100 to shift from the open jaws configuration to the closed jaws configuration. In some embodiments, actuating a first trigger can cause the upper jaw member 104 to pivot toward the lower jaw member 106. In some embodiments, actuating a first trigger can cause the lower jaw member 106 to pivot toward the upper jaw member 104. In some embodiments, actuating a second trigger can cause the suture passer 100 to shift from the needle undeployed to the needle deployed configuration. In some embodiments, actuating a second trigger can cause the needle to deploy from the lower jaw member 106. In some embodiments, the trigger 110 can be a button, a sliding component, or a computer-controlled component. The needle deployed position can be a retracted position. The needle undeployed position can be an engaged position.

Figure 1B:
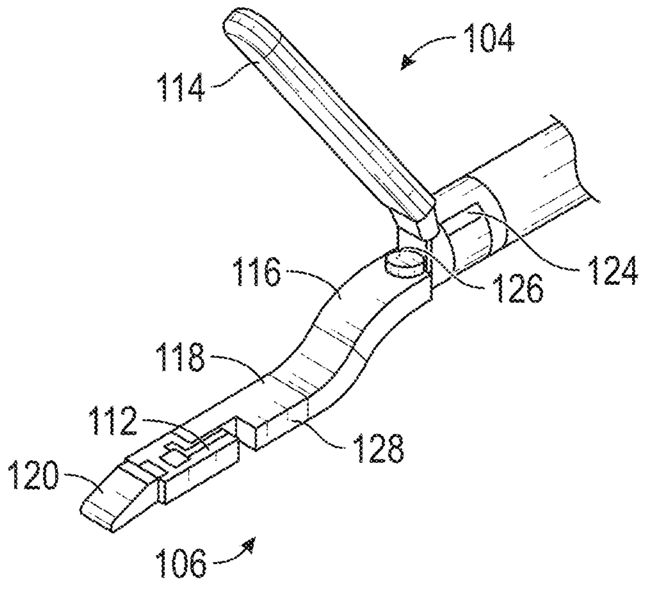
FIG. 1B shows an example of the upper jaw member and lower jaw member of the suture passer of FIG. 1A.

FIG. 1B shows an example of the upper jaw member 104 and lower jaw member 106 of the suture passer 100 of FIG. 1A. In certain examples, the upper jaw member 104 can be a substantially straight arm. In some embodiments, the upper jaw member 104 can be curved. The upper jaw member 104 can be connected to a distal end of the elongate member 102 by a hinge 124. The trigger 110 can cause the upper jaw member 104 to rotate about the hinge 124. The trigger 110 can cause the closing link 126 to move (e.g., distally towards the distal end of the suture passer 100, or proximally away from the distal end of the suture passer 100). In some embodiments, the trigger 110 can be coupled with the closing link 126. In some embodiments, the trigger 110 can be coupled with an internal component that is coupled with the closing link 126. The trigger 110 can shift the closing link 126 to an unactuated position to an actuated position. The closing link 126 can be coupled with the upper jaw member 104. Movement of the closing link 126 can cause the upper jaw member 104 to pivot about the hinge 124. The upper jaw member 104 can include a slot 114 for the needle 112, or tissue penetrator, to pass through. The upper jaw member 104 can be capable of angular movement relative to the elongate member 102. The lower jaw member 106 can include a curved portion 116 extending from a distal end of the elongate member 102. The curved portion 116 can curve downward or away from the upper jaw member 104. The curved portion 116 can offset the straight portion 118 of the lower jaw member 106 from the centerline of the elongate member 102. In some embodiments, the curved portion 116 can offset the straight portion 118 of the lower jaw member 106 from the centerline of the elongate member 102 by 3 mm. In some embodiments, the curved portion 116 can offset the straight portion 118 of the lower jaw member 106 from the centerline of the elongate member 102 by 0 to 5 mm. In some embodiments, the curved portion 116 can offset the straight portion 118 of the lower jaw member 106 from the centerline of the elongate member 102 by 0 to 10 mm, or any value, approximate value, or range of values within the foregoing ranges. The lower jaw member 106 can be offset from the elongate member 102. The lower jaw member 106 can be offset from the upper jaw member 104. The lower jaw member 106 can be offset from the hinge 124. In some embodiments, the upper jaw member 104 can be offset from the hinge 124.

The lower jaw member 106 can include a straight portion 118 extending from a distal end of the curved portion 116. The straight portion 118 can extend substantially straight. The straight portion 118 can be parallel with the elongate member 102.

The straight portion 118 of the lower jaw member 106 can include a suture loader 128, or a suture router. A suture can be routed through the suture loader 128 to the needle 112. The suture loader 128 can be an opening in the side of the lower jaw member 106. The suture loader 128 can be an opening that extends to or near the center of the lower jaw member 106. For example, the suture loader 128 can include a notch in the side of the lower jaw member 106 and a slot perpendicular to the notch. Routing the suture in the suture loader 128 can include pulling the suture through the notch in the side of the lower jaw member 106 and pulling the suture through the slot perpendicular to the notch. The slot perpendicular to the notch can be aligned with the needle 112. The slot perpendicular to the notch can be in the center of the lower jaw member 106. In some embodiments, a suture can be routed through the side opening of the suture loader 128 to the center of the lower jaw member 106. In some embodiments, a suture can be routed through the side opening of the suture loader 128 to the needle 112.

The lower jaw member 106 can include a shoulder 120. The shoulder 120 can be a ridge or protrusion at a distal end of the straight portion 118 of the lower jaw member 106. In some embodiments, the needle 112 can be deployed such that it abuts the shoulder 120. In some embodiments, the needle 112 can be deployed such that it abuts the shoulder 120 and directed across the tissue. In some embodiments, the shoulder 120 can direct the needle 112 when the needle 112 is deployed. In some embodiments, the needle 112 can abut the shoulder 120 when deployed and be redirected toward the first jaw member 104. In some embodiments, the needle 112 can abut the shoulder 120 when deployed and be directed upward, which can be a direction from the lower jaw member 106 towards the upper jaw member 104. In some embodiments, the needle 112 can break at a notch to allow the needle to bend and/or protrude from the lower jaw member 106. The needle 112 can be back fed through the lower jaw member 106. In some embodiments, the needle 112 can be back fed through the lower jaw member 106 through a tight S-Bend. In some embodiments, the S-Bend can be lengthened or the offset between the jaw members 104, 106 can be reduced.

Figure 2A:
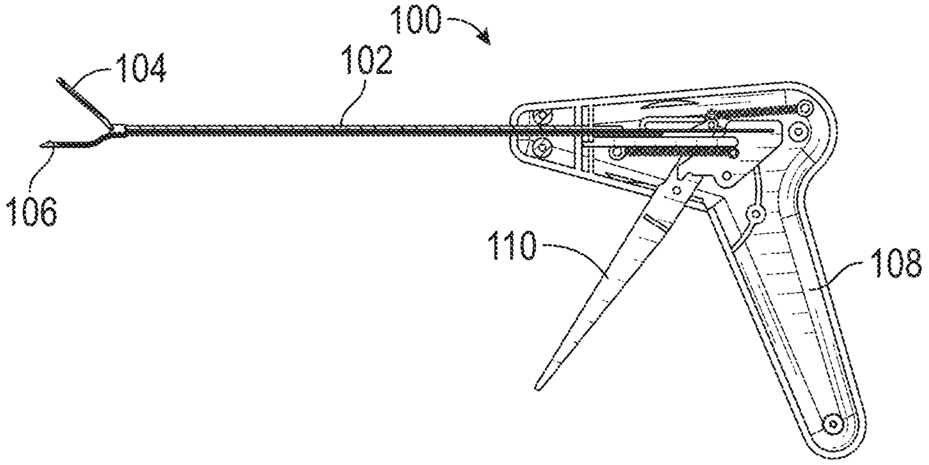
FIG. 2A shows a cross-sectional view of the suture passer of FIG. 1A in the open jaws configuration.
Figure 2B:
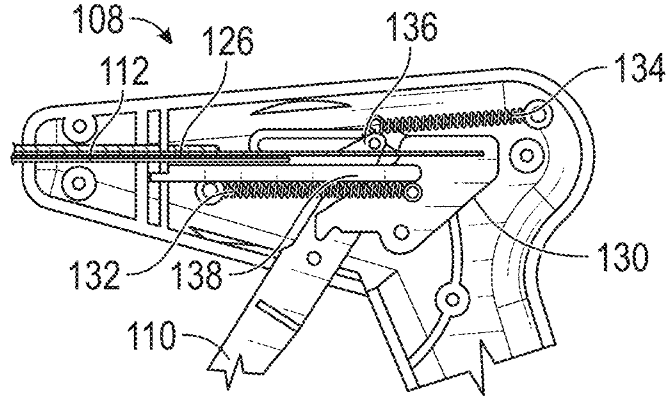
FIG. 2B shows a cross-sectional view of the handle of a suture passer of FIG. 1A in the open jaws configuration.
Figure 2C:
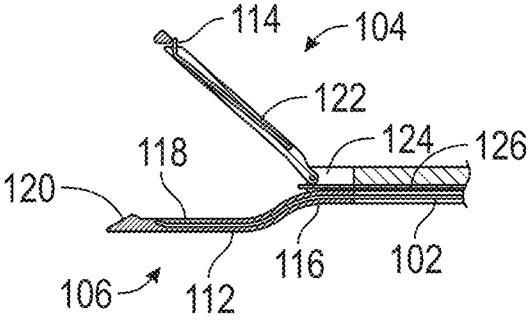
FIG. 2C shows a cross-sectional view of the jaw members of a suture passer of FIG. 1A in the open jaws configuration.

FIG. 2A shows a cross-sectional view of the suture passer 100 of FIG. 1A in the open jaws configuration. FIG. 2B shows a cross-sectional view of the handle 108 of a suture passer 100 of FIG. 1A in the open jaws configuration. FIG. 2C shows a cross-sectional view of the jaw members 104, 106 of a suture passer 100 of FIG. 1A in the open jaws configuration.

As shown in FIG. 2A, in the open jaws configuration, the trigger 110 can be unactuated or uncompressed. In the open jaws configuration or needle undeployed configuration, the needle 112 can be undeployed.

As shown in FIG. 2B, in the open jaws configuration, the closing link 126 can be unactuated. The closing link 126 can keep the jaw members 104, 106 open.

The trigger 110 can be coupled with or positioned adjacent to a closing cam 130. The closing cam 130 can be coupled with a proximal end of the closing link 126. The closing cam 130 can be connected to a spring 132. The spring 132 can couple the closing cam 130 to the handle 108. Actuating the trigger 110 can cause the closing cam 130 to move such that the closing link 126 is retracted (e.g., moved proximally). Retracting the closing link 126, to an actuated position, can cause the upper jaw member 104 to close, or move toward the lower jaw member 106. Releasing the trigger 110 can cause the spring 132 to cause the closing cam 130 to return to its original position. Movement of the closing cam 130 to its original position can cause the closing link 126 to return to its original position, opening the jaws by moving the upper jaw member 104 away from the lower jaw member 106.

The trigger 110 can be connected to an extension spring 134. The extension spring 134 can couple the trigger 110 to the handle 108. The extension spring 134 can cause the trigger 110 to return to its original position when the trigger 110 is released. The trigger 110 can be coupled with or positioned adjacent to a needle termination 136. The needle termination 136 can be coupled with a proximal end of the needle 112. Actuating the trigger 110 can cause the needle termination 136 to move such that the needle 112 is pushed forward (e.g., distally). Pushing the needle 112 forward can cause the needle 112 to protrude from the lower jaw member 106. In some embodiments, releasing the trigger 110 can cause the needle termination 136 to return to its original position (e.g., move proximally). In some embodiments, releasing the trigger 110 can cause the needle 112 to retract into the lower jaw member 106. In some embodiments, the needle termination 136 can remain in place when the trigger 110 is released. In some embodiments, the needle 112 can remain protruded from the lower jaw member 106 when the trigger 110 is released.

The needle termination 136 can be configured such that partially actuating the trigger 110 does not cause the needle termination 136 to move. For example, the trigger 110 can include a hole which can move around the needle termination 136. Actuating the trigger 110 further can cause the needle termination 136 to move as the proximal end of the hole in the trigger 110 can push the needle termination 136 forward. Therefore, partially actuating the trigger 110 can cause the jaw members 104, 106 to close without causing the needle 112 to protrude. Actuating the trigger 110 further, or fully actuating the trigger 110, can cause the needle 112 to protrude. The trigger 110 can be a two-stage trigger. The first stage of the trigger 110 can include closing the jaw members 104, 106. The second stage of the trigger 110 can include protruding the needle 112. In some embodiments, the trigger 110 can include a protrusion that only causes the cam 130 to move (e.g., rotate relative to the handle 108) when the trigger 110 moves from an unactuated configuration (e.g., the jaws 104, 106 are open) to a partially actuated configuration (e.g., the jaws 104, 106 are closed but the needle 112 is not yet deployed). The protrusion on the trigger 110 may be shaped to maintain the cam 130 in its rotated position, without further rotating the cam 130, when the trigger 110 moves from a partially actuated configuration to a fully actuated configuration (e.g., the jaws 104, 106 are closed and the needle 112 is fully deployed). The trigger 110 may no longer cause the cam 130 to rotate when the trigger 110 moves from partially actuated to fully actuated, which may allow the needle 112 to be deployed without causing one or both jaws 104, 106 to continue moving relative to each other.

The closing cam 130 and/or the handle 108 can be coupled with a guide plate 138. The guide plate 138 can provide a movement path for the needle termination 136. For example, the guide plate 138 can allow the needle termination 136 to move straight toward the elongate member 102 when the trigger 110 is actuated. The guide plate 138 can prevent bending of the proximal end of the needle 112.

In some embodiments, the handle 108 can include ribs (not shown) to support the proximal end of the needle 112. For example, the ribs can be above and/or below the proximal end of the needle 112. In some embodiments, the guide plate 138 can include rails along which the needle 112 can move. In some embodiments, the handle 108 can include a ribbon (not shown) to assist in actuating the upper jaw member 104. For example, the ribbon can pull the upper jaw member 104 toward and away from the lower jaw member 106.

As shown in FIG. 2C, in the open configuration, the upper jaw member 104 can extend at an upward angle from the distal end of the elongate member 102. The upper jaw member 104 can extend away from the lower jaw member 106. The upper jaw member 104 can be positioned at an angle of 45 degrees from the elongate member 102. In some embodiments, the upper jaw member 104 can be positioned at an angle of 30-60 degrees from the elongate member 102. In some embodiments, the upper jaw member 104 can be positioned at an angle of 10-90 degrees from the elongate member 102, or any value, approximate value, or range of values in the foregoing ranges.

In some embodiments, the needle 112 can be housed partially or entirely in the lower jaw member 106 when undeployed. In some embodiments, the needle 112 can be housed partially or entirely in the elongate member 102 when undeployed. In some embodiments, the needle 112 can protrude slightly from the lower jaw member 106 when undeployed. In some embodiments, the distal end of the needle 112 can be sheathed by the lower jaw member 106 when undeployed.

The upper jaw member 104 can include a suture retainer 122, for example disposed inside the upper jaw member 104. The suture retainer 122 can grip the suture as it passes through the slot 114 of the upper jaw member 104. The suture retainer 122 can hold a distal end of the suture. Once the suture is passed across a tissue, the suture passer 100 can be returned to the open jaws configuration. The suture retainer 122 can hold the suture while the upper jaw member 104 pivots away from the lower jaw member 106. In some embodiments, the suture retainer 122 can grip the suture by gripping the suture between the suture retainer 122 and a portion of the upper jaw member 104. For example, the needle 112 can cause the suture to pass through (e.g., between) the suture retainer 122 and a portion of the upper jaw member 104, and the suture retainer 122 can grab or hold the suture by pressing the suture against the upper jaw member 104 to prevent the suture from slipping out from between the suture retainer 122 and the upper jaw member 104. In some embodiments, the suture retainer 122 can include an opening through which the suture can pass, so that the suture retainer 122 can hold or grab the suture within the opening. In some embodiments, the suture retainer 122 can be angled upwards (e.g., in a direction away from the lower jaw member 106), which may allow the suture to be pulled upwards from the suture retainer 122 without causing damage to the suture, and which may help prevent the suture from slipping downwards towards the lower jaw member

106. In some embodiments, the suture retainer 122 prongs, teeth, or barbs at a distal end of the suture retainer 122 to help grab the suture.

Figure 3A:
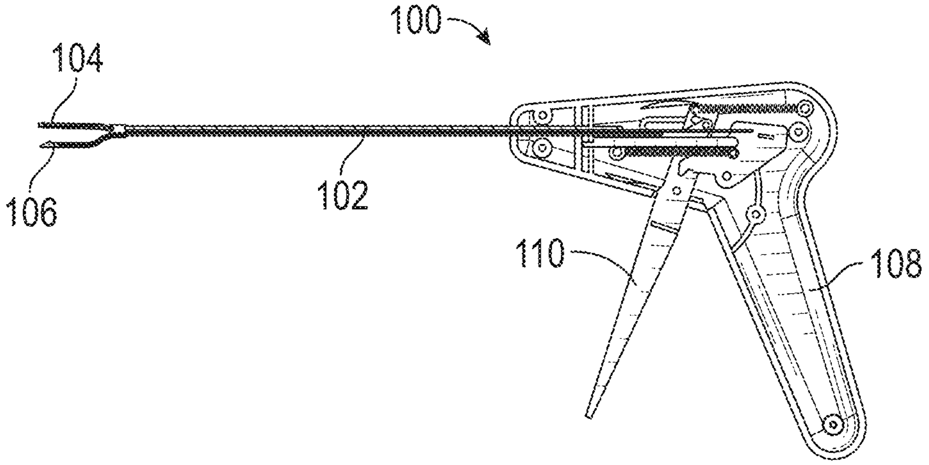
FIG. 3A shows a cross-sectional view of the suture passer of FIG. 1A in the closed jaws configuration.
Figure 3B:
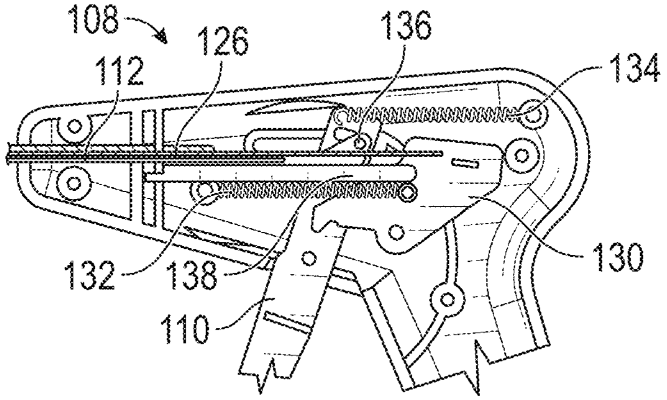
FIG. 3B shows a cross-sectional view of the handle of a suture passer of FIG. 1A in the closed jaws configuration.
Figure 3C:
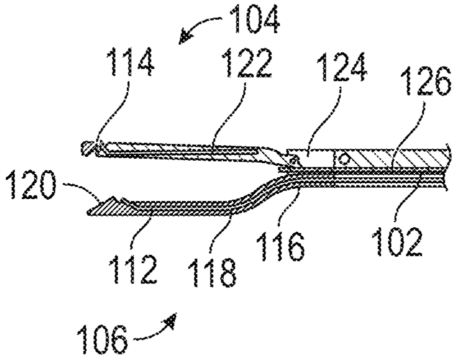
FIG. 3C shows a cross-sectional view of the jaw members of a suture passer of FIG. 1A in the closed jaws configuration.

FIG. 3A shows a cross-sectional view of the suture passer 100 of FIG. 1A in the closed jaws configuration. FIG. 3B shows a cross-sectional view of the handle 108 of a suture passer 100 of FIG. 1A in the closed jaws configuration. FIG. 3C shows a cross-sectional view of the jaw members 104, 106 of a suture passer 100 of FIG. 1A in the closed jaws configuration.

As shown in FIG. 3A, in the closed jaws configuration, the trigger 110 can be partially actuated or partially compressed. In the closed jaws configuration or needle undeployed configuration, the needle 112 can be undeployed.

As shown in FIG. 3B, in the closed jaws configuration, the closing link 126 can be actuated. The closing link 126 can keep the jaw members 104, 106 closed. The suture passer 100 can function as described with respect to FIG. 2B.

As shown in FIG. 3C, in the closed jaws configuration, the upper jaw member 104 can be substantially horizontal. The upper jaw member 104 can be substantially parallel to the elongate member 102. The upper jaw member 104 can extend from the elongate member 102 at an angle of 0-10 degrees relative to the elongate member 102. In some embodiments, the upper jaw member 104 can extend from the elongate member 102 at an angle of 0-20 degrees relative to the elongate member 102, or any value, approximate value, or range of values within the foregoing ranges. The space between the upper jaw member 104 and the lower jaw member 106 can be smaller in the closed jaws configuration than in the open jaws configuration.

In the closed jaws configuration, the upper jaw member 104 and the lower jaw member 106 can pinch a layer of tissue. The upper jaw member 104 can engage the top of a layer of tissue. The lower jaw member 106 can engage the bottom of a layer of tissue.

Figure 4A:
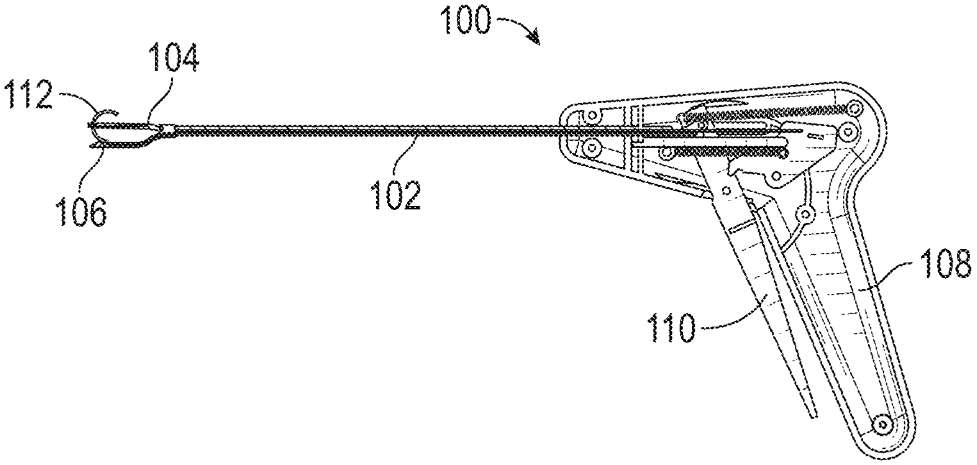
FIG. 4A shows a cross-sectional view of the suture passer of FIG. 1A in the needle deployed configuration.
Figure 4B:
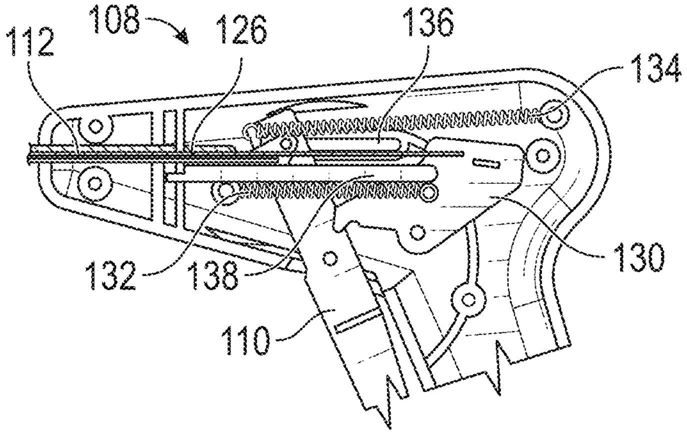
FIG. 4B shows a cross-sectional view of the handle of a suture passer of FIG. 1A in the needle deployed configuration.
Figure 4C:
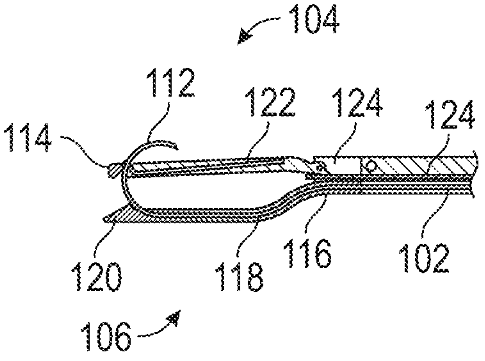
FIG. 4C shows a cross-sectional view of the jaw members of a suture passer of FIG. 1A in the needle deployed configuration.

FIG. 4A shows a cross-sectional view of the suture passer 100 of FIG. 1A in the needle deployed configuration. FIG. 4B shows a cross-sectional view of the handle 108 of a suture passer 100 of FIG. 1A in the needle deployed configuration. FIG. 4C shows a cross-sectional view of the jaw members 104, 106 of a suture passer 100 of FIG. 1A in the needle deployed configuration.

As shown in FIG. 4A, in the needle deployed configuration, the trigger 110 can be actuated or compressed. In the needle deployed configuration, the needle 112 can be deployed through the first jaw member 104.

As shown in FIG. 4B, in the needle deployed configuration, the closing link 126 can be actuated. The closing link 126 can keep the jaw members 104, 106 closed. The suture passer 100 can function as described with respect to FIG. 2B.

As shown in FIG. 4C, in the needle deployed configuration, the needle 112 or tissue penetrator can extend from the lower jaw member 106. The needle 112 can be made of a flexible material, for example nitinol. In some embodiments, the needle 112 may be a metal, polymeric, alloy, ceramic, composite, or other material. The needle 112 may have a sharp distal end. The needle 112 can have a suture engagement feature near the distal end of the needle 112. The suture engagement feature may be a hole or clip configured to couple with a suture.

The needle 112 can extend from the straight portion 118 of the lower jaw member 106. The needle 112 can pass through the slot 114 in the upper jaw member 104. The needle 112 can curve downward (e.g., in a direction towards the lower jaw member 106) at the distal end of the needle 112. The downward curve of the needle 112 can be caused by a bias in the needle 112. The downward curve of the needle 112 can be caused by the force, velocity, and/or momentum undergone during deployment. Advantageously, the downward curve of the needle 112 can reduce the risk of damage to surrounding tissue.

Figure 5:
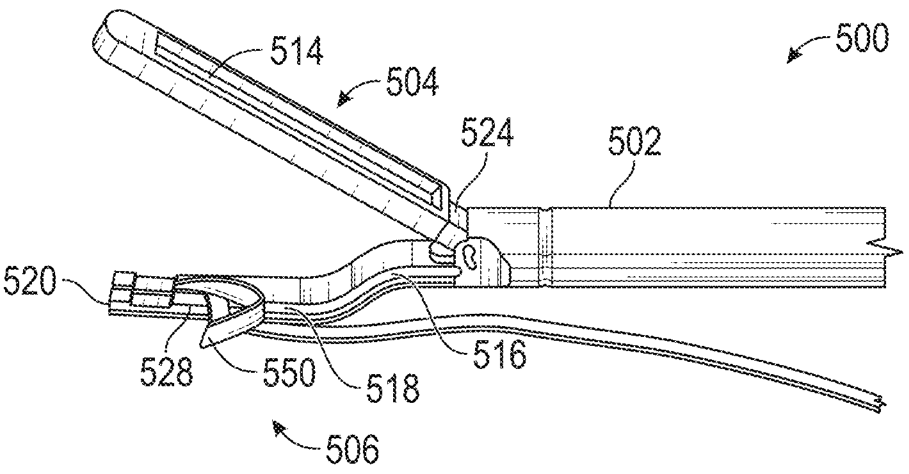
FIG. 5 shows an example of a suture passer with a suture attached.

FIG. 5 shows an example of a suture passer 500 with a suture 550 attached. The suture passer 500 can be similar to the suture passer 100 shown in FIG. 1A.

The suture passer 500 can include an elongate member 502. The suture passer 500 can include an upper jaw member 504 and a lower jaw member 506 extending from the distal end of the elongate member 502. The upper jaw member 504 can include a slot 514 which a needle or tissue penetrator can pass through. The lower jaw member 506 can include a curved portion 516 extending from the distal end of the elongate member. The lower jaw member 506 can include a straight portion 518 extending from the distal end of the curved portion 516. The straight portion 518 of the lower jaw member 506 can include a suture loader 528 for retaining the suture. The needle can be disposed within the suture loader 528 when not deployed. The straight portion 518 of the lower jaw member 506 can include a shoulder 520 at the distal end. The shoulder 520 can direct the needle toward the upper jaw member 504 when deployed.

In some embodiments, a user can form a loop at the end of a suture 550. The user can route the suture 550 through the suture loader 528 such that the suture contacts the needle. In some embodiments, the user can route the suture 550 through a notch in the side of the lower jaw member 106. In some embodiments, the user can route the suture through slot perpendicular to the notch in the side of the lower jaw member 506. In some embodiments, the user can route the suture 550 through a notch at a distal end of the lower jaw member 506. In some embodiments, the user can route the suture through a slot connected to the notch in the lower jaw member 106. In some embodiments, the user can route the loop through the suture loader 528 such that the loop contacts the needle. The user can position the upper jaw member 504 and the lower jaw member 506 to surround a layer of tissue. The user can engage a trigger to close the jaw members 504, 506 around the layer of tissue. The user can further engage the trigger, or engage another trigger, to deploy the needle across the tissue. The needle can carry the suture 550 across (e.g., through) the tissue. In some embodiments, the distal end of the suture 550 can remain on the first side of the tissue with the lower jaw member 506. In some embodiments, the distal end of the suture can pass to the second side of the tissue with the upper jaw member 504. The position of the distal end of the suture 550 can depend on the point at which the suture is loaded in the suture loader 528.

Once the suture 550 is passed across the tissue, the user can release the trigger. In some embodiments, the user can actuate a trigger to shift the suture passer 500 from the needle deployed position to the needle undeployed position. In some embodiments, the user can actuate a trigger to shift the suture passer 500 from the closed jaws position to the open jaws position. The upper jaw member 504 can retain the suture 550 when the jaws open. The suture 550 can be routed from a first side of the tissue to the second side of the tissue.

Figure 6A:
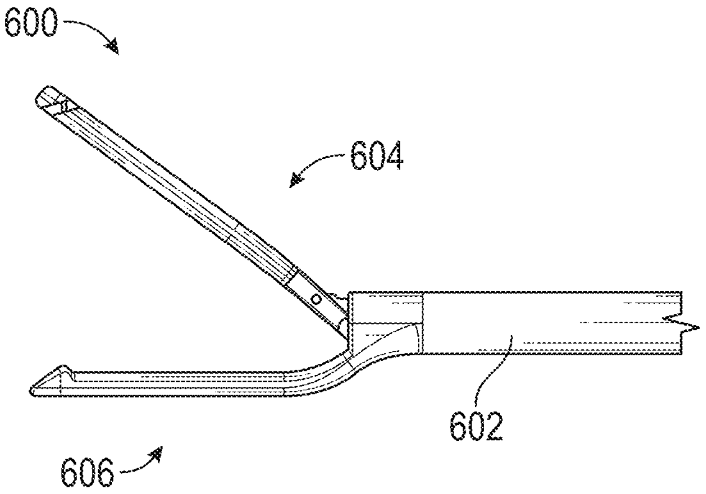
FIG. 6A shows another example of a suture passer in a jaws open configuration.
Figure 6B:
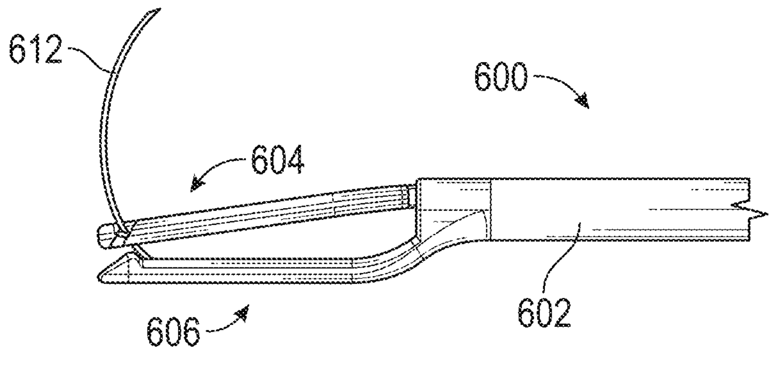
FIG. 6B shows the example of the suture passer of FIG. 6A in a jaws closed, needle deployed configuration.
Figure 6C:
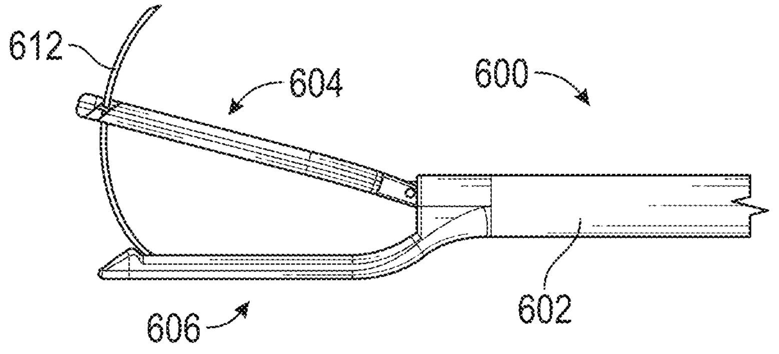
FIG. 6C shows the example of the suture passer of FIG. 6A in a jaws open, needle deployed configuration.

FIG. 6A shows another example of a suture passer 600 in a jaws open configuration. FIG. 6B shows an example similar to the suture passer 600 of FIG. 6A in a jaws closed, needle deployed configuration. FIG. 6C shows the example of the suture passer 600 of FIG. 6A in a jaws open, needle deployed configuration. The suture passer 600 can be similar to the suture passer 100 of FIGS. 1A-1B, 2A-C, 3A-C, and 4A-C and the suture passer 500 of FIG. 5.

As shown in FIG. 6A, the upper jaw 604 can be inclined away from the lower jaw member 606 with respect to the horizontal axis, or the axis parallel to the elongate member 602, in the jaws open configuration. As shown in FIG. 6B, the upper jaw 604 can be declined toward the lower jaw member 606 in the jaws closed configuration. As shown in FIG. 6C, the upper jaw 604 can be inclined away from the lower jaw member 606 in the jaws open, needle deployed configuration.

In some implementations, the needle 612 can curve downward at an angle of between 10 degrees and 45 degrees when deployed. In some implementations, the needle 612 can curve downward at an angle of between 5 degrees and 60 degrees when deployed. In some implementations, the needle 612 can curve downward at an angle of between 1 degree and 120 degrees when deployed, or any value, approximate value, or range of values within the foregoing ranges. In some implementations, the needle 612 can curve downward at an angle of greater than 120 degrees when deployed. The needle 612 can have a length of 18.5 mm. In some implementations, the needle 612 can have a length of 15-20 mm. In some implementations, the needle 612 can have a length of 10-30 mm, or any value, approximate value, or range of values within the foregoing ranges. In some implementations, the needle 612 length can vary based on the procedure. For example, a suture passer for a meniscus may have a needle that is shorter than a suture passer for a rotator cuff. In some embodiments, a suture passer for a rotator cuff may have a needle with a length 3 mm greater than the needle 612 for a meniscus operation. In some embodiments, a suture passer for a rotator cuff may have a needle with a length 1-5 mm greater than the needle 612 for a meniscus operation, or any value, approximate value, or range of values within the foregoing ranges.

The elongate member 602 can have a diameter of 5.16 mm. In some implementations, the elongate member 602 can have a diameter of 4-7 mm. In some implementations, the elongate member 602 can have a diameter of 1-10 mm. In some implementations, the elongate member 602 can have a diameter of between 0.5 mm and 20 mm. In some implementations, the elongate member 602 can have a diameter of between 0.05 mm and 30 mm, or any value, approximate value, or range of values within the foregoing range.

The lower jaw 606 can have a length along the horizontal axis, or the axis parallel to the elongate rod 602, of 26 mm. In some implementations, the lower jaw 606 can have a length of 20-30 mm. In some implementations, the lower jaw 606 can have a length of 10-40 mm, or any value, approximate value, or range of values within the foregoing ranges.

The bottom of the lower jaw member 606 can be offset from the bottom of the elongate member 602 by 3.4 mm. In some implementations, the bottom of the lower jaw member 606 can be offset from the bottom of the elongate member 602 by 2-5 mm. In some implementations, the bottom of the lower jaw member 606 can be offset from the bottom of the elongate member 602 by 1-8 mm. In some implementations, the bottom of the lower jaw member 606 can be offset from the bottom of the elongate member 602 by between 0.5 mm and 20 mm. In some implementations, the bottom of the lower jaw member 606 can be offset from the bottom of the elongate member 602 by between 0.05 mm and 30 mm, or any value, approximate value, or range of values within the foregoing range.

As shown with respect to FIG. 6A, at a maximum jaw opening, or in a fully opened position, the distance on the vertical axis between the distal end of the lower jaw member 606 and the vertically adjacent portion of the upper jaw member 604 can be 18 mm. In some embodiments, in a fully opened position, the distance on the vertical axis between the distal end of the lower jaw member 606 and the vertically adjacent portion of the upper jaw member 604 can be 15-20 mm. In some embodiments, in a fully opened position, the distance on the vertical axis between the distal end of the lower jaw member 606 and the vertically adjacent portion of the upper jaw member 604 can be 10-30 mm. In some embodiments, in a fully opened position, the distance on the vertical axis between the distal end of the lower jaw member 606 and the vertically adjacent portion of the upper jaw member 604 can be 5-40 mm, or any value, approximate value, or range of values within the foregoing ranges.

As shown with respect to FIG. 6B, at a minimum jaw opening, or in a jaws closed position, the distance on the vertical axis between the distal end of the lower jaw member 606 and the vertically adjacent portion of the upper jaw member 604 can be 1.3 mm. In some embodiments, in a jaws closed position, the distance on the vertical axis between the distal end of the lower jaw member 606 and the vertically adjacent portion of the upper jaw member 604 can be 1-2 mm. In some embodiments, in a jaws closed position, the distance on the vertical axis between the distal end of the lower jaw member 606 and the vertically adjacent portion of the upper jaw member 604 can be 0.5-5 mm. In some embodiments, in a jaws closed position, the distance on the vertical axis between the distal end of the lower jaw member 606 and the vertically adjacent portion of the upper jaw member 604 can be 0.1-10 mm, or any value, approximate value, or range of values within the foregoing ranges. The needle 612 can extend 17 mm beyond the upper jaw member 604. In some embodiments, the needle 612 can extend 15-20 mm beyond the upper jaw member 604. In some embodiments, the needle 612 can extend 10-30 mm beyond the upper jaw member 604, or any value, approximate value, or range of values within the foregoing ranges.

As shown with respect to FIG. 6C, at a maximum jaw opening with the needle deployed, or in a jaws open, needle deployed position, the distance on the vertical axis between the distal end of the lower jaw member 606 and the vertically adjacent portion of the upper jaw member 604 can be 10 mm. In some embodiments, in a jaws open, needle deployed position, the distance on the vertical axis between the distal end of the lower jaw member 606 and the vertically adjacent portion of the upper jaw member 604 can be 5-15 mm. In some embodiments, in a jaws open, needle deployed position, the distance on the vertical axis between the distal end of the lower jaw member 606 and the vertically adjacent portion of the upper jaw member 604 can be 1-20 mm. In some embodiments, in a jaws open, needle deployed position, the distance on the vertical axis between the distal end of the lower jaw member 606 and the vertically adjacent portion of the upper jaw member 604 can be 0.5-30 mm, or any value, approximate value, or range of values within the foregoing ranges. The needle 612 can extend 8.5 mm beyond the upper jaw member 604. In some embodiments, the needle 612 can extend 7-10 mm beyond the upper jaw member 604. In some embodiments, the needle 612 can extend 3-15 mm beyond the upper jaw member 604. In some embodiments, the needle 612 can extend 1-20 mm beyond the upper jaw member 604, or any value, approximate value, or range of values within the foregoing ranges.

Figure 7:
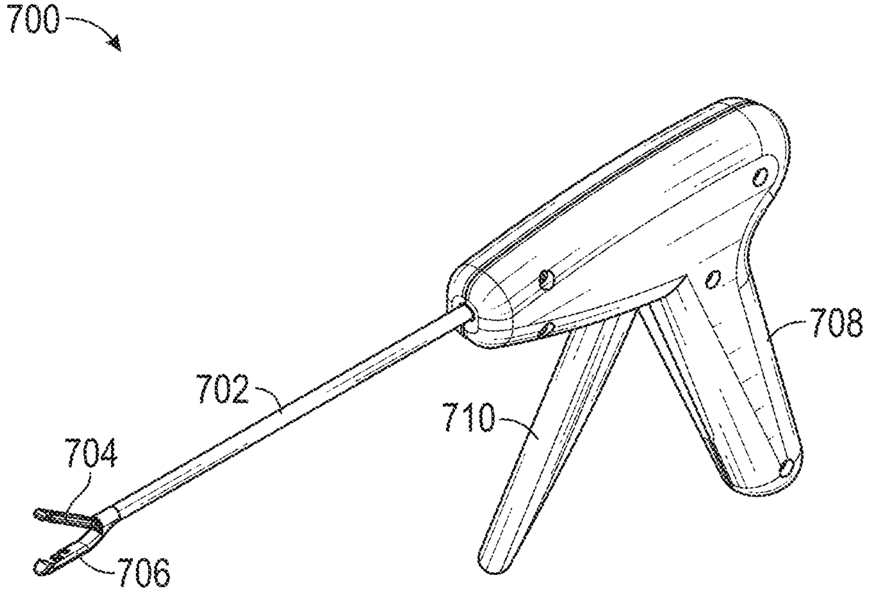
FIG. 7 shows a perspective view of an example of a suture passer.

FIG. 7 shows a perspective view of another example of a suture passer 700. The suture passer 700 can be similar to the suture passer 100 of FIGS. 1A-1B, 2A-C, 3A-C, and 4A-C, suture passer 500 of FIG. 5, and/or suture passer 600 of FIGS. 6A-C, and can have any of the same or similar elements, components, or features. The suture passer 100 of FIGS. 1A-1B, 2A-C, 3A-C, and 4A-C, suture passer 500 of FIG. 5, and/or suture passer 600 of FIGS. 6A-C can be similar to suture passer 700 and can have any of the same or similar elements, components, or features.

Suture passer 700 can include a handle 708, an elongate member 702 that can extend from the handle 708, an upper jaw member 704 and a lower jaw member 706 at a distal end of the elongate member 702, and a trigger 710 that can cause at least one of the upper jaw member 704 and the lower jaw member 706 to move with respect to the other. The trigger 710, or another trigger, can control deployment of a tissue penetrator (e.g., needle 712). The trigger 710 can shift the suture passer 700 between the open jaws configuration and the closed jaws configuration. The trigger 710 can shift the suture passer 700 between the needle undeployed and the needle deployed configuration.

Figure 8:
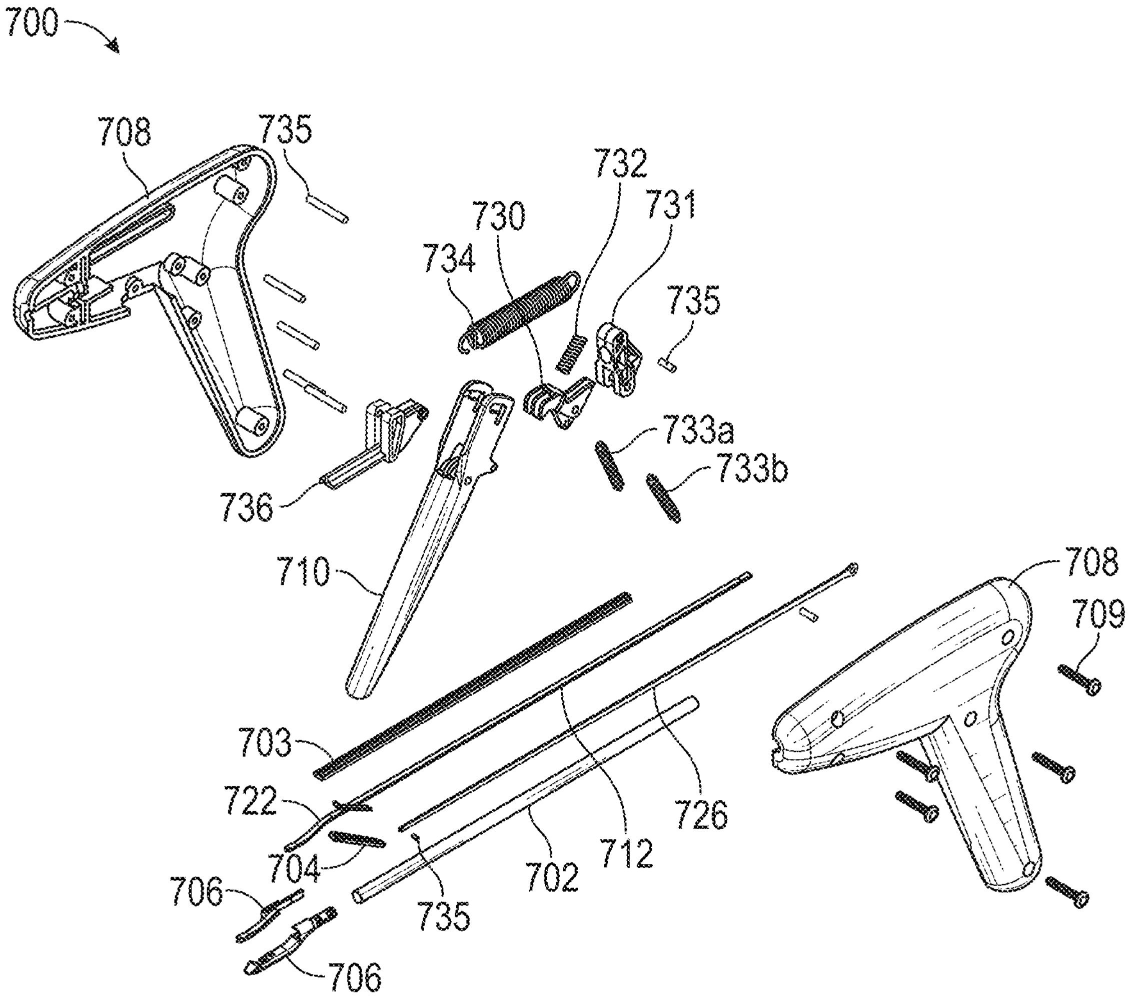
FIG. 8 shows an exploded view of the suture passer of FIG. 7.

FIG. 8 illustrates an exploded view of a suture passer 700. The suture passer 700 can include, for example, a handle 708, a trigger 710, an elongate member 702, an upper jaw member 704, a lower jaw member 706, a needle 712, a needle termination 736, and a closing link 726. The suture passer 700 can include a shaft insert 703, which can be positioned within the elongate member 702 and can help guide the needle termination 736 as the needle termination moves distally and proximally within the handle 708. The suture passer 700 can include a spring 732, a yoke 731, and a closing cam 730 which can engage with the trigger 710 and the closing link 726 to cause the jaws 704, 706 to open and close. The suture passer 700 can include extension springs 733*a*, 733*b* which can couple the trigger 710 to the handle 708. The suture passer 700 can include pins 735 and/or screws 709 that can couple various components within the handle 708. The suture passer 700 can include spring 734 which can couple the needle termination 736 to the handle 708. A suture retainer 722 can be used to grab or retain the suture through the upper jaw 704.

FIGS. 9A-14B illustrate cross-sectional views of a suture passer 700 with the upper jaw member 704 and the lower jaw member 706 moving between an open configuration and a closed configuration, and the needle 712 moving between an undeployed configuration and a deployed configuration. FIGS. 9A, 10A, 11A, 12A, 13A and 14A illustrate cross-sectional views of the suture passer 700, and FIGS. 9B, 10B, 11B, 12B, 13B, and 14B illustrate cross-sectional views of the trigger 110 interacting with the closing cam 730, among other things.

Figure 9A:
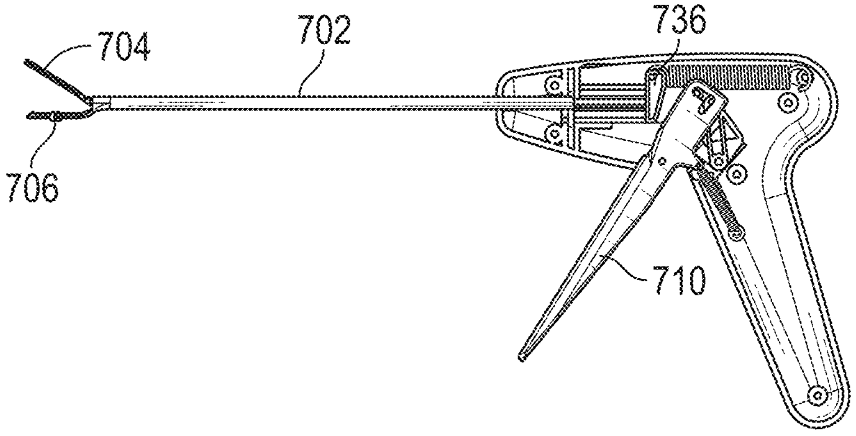
FIGS. 9A-9B show cross-sectional views of a suture passer in an open jaws configuration and a needle undeployed configuration.
Figure 9B:
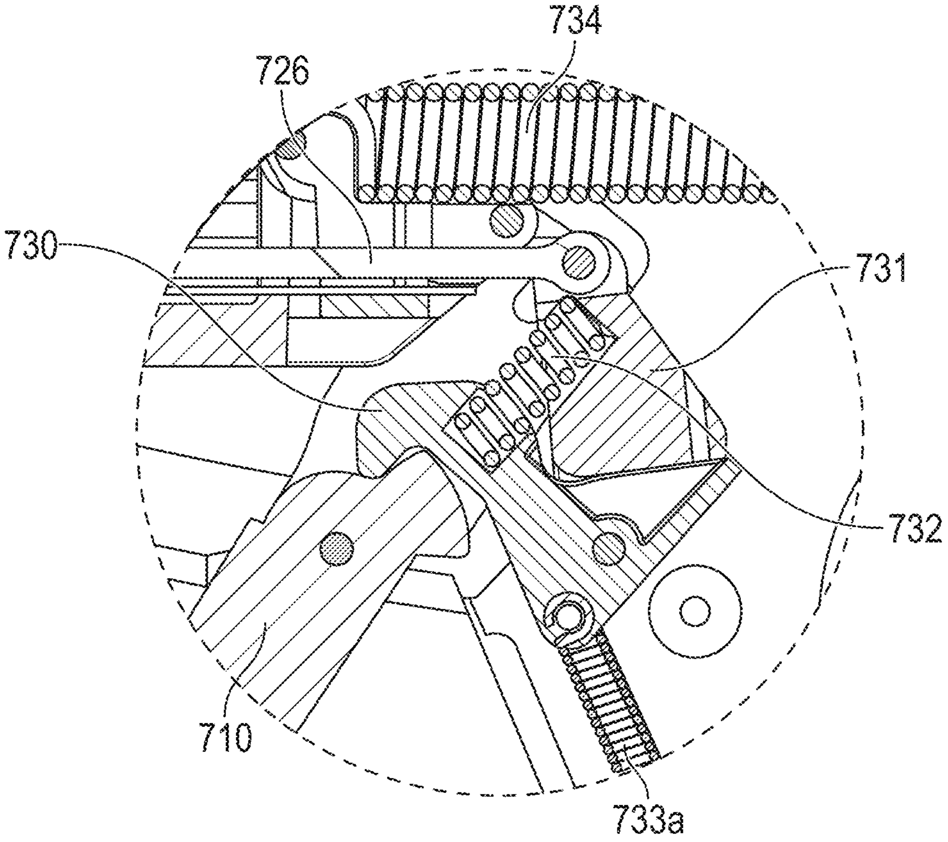

FIGS. 9A-9B illustrate cross-sectional views of a suture passer 700 with the upper jaw member 704 and lower jaw member 706 in an open configuration and the needle 712 in an undeployed configuration. The trigger 710 can be positioned against the closing cam 730. The spring 732 can couple the closing cam 730 to the yoke 731. The closing link 726 can be coupled to the yoke 731. In some embodiments, actuating the trigger 710 can cause the closing cam 730 to move the yoke 731, which can cause the closing link 726 to move, which can cause the upper jaw member 704 to move relative to the lower jaw member 706. The one or more extension springs 733*a*, 733*b* can couple the trigger 710 to the handle 708, which may bias the trigger 710 such that the trigger 710 is in an unactuated configuration and the suture passer 700 is in an open configuration.

Figure 10A:
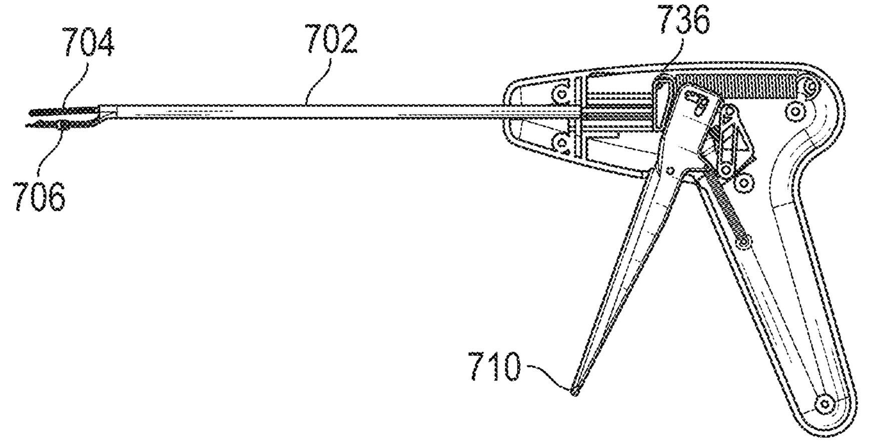
FIGS. 10A-10B show cross-sectional views of a suture passer in a closed jaws configuration and a needle undeployed configuration.
Figure 10B:
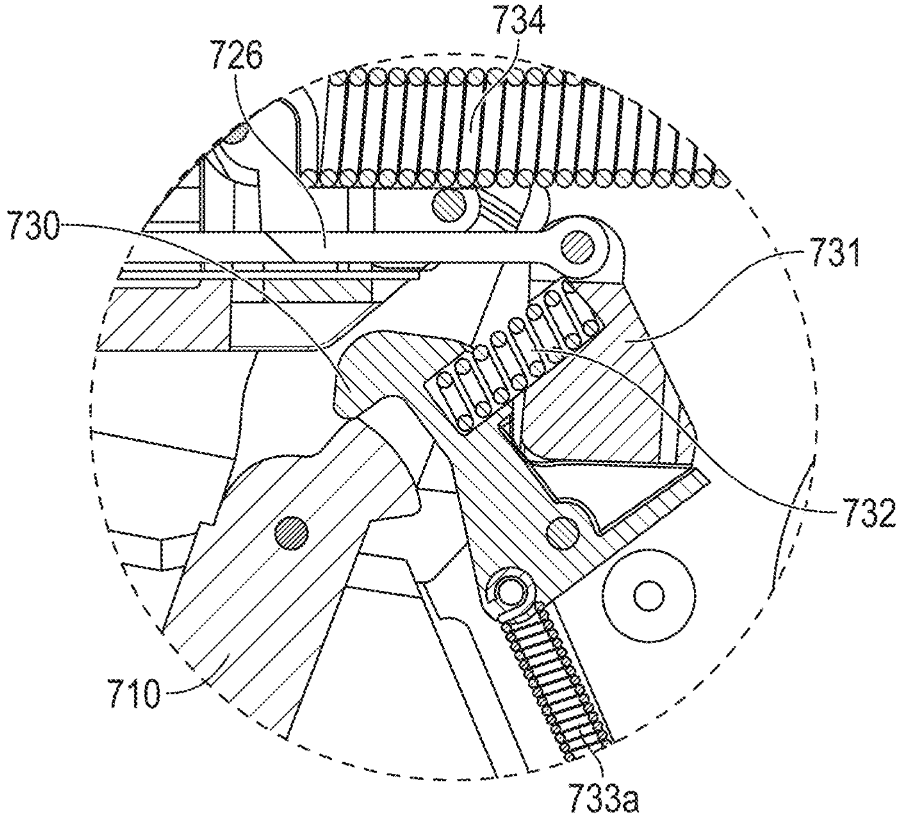

FIGS. 10A-10B illustrate cross-sectional views of a suture passer 700 with the upper jaw member 704 and lower jaw member 706 in a closed configuration and the needle 712 in an undeployed configuration. The trigger 710 can engage the closing cam 730, which may cause the yoke 731 to rotate (e.g., relative to the handle 708), which may cause the closing link 726 to move proximally (e.g., in a direction away from the distal end of the elongate member 702), which may cause the upper jaw member 704 to move relative to the lower jaw member 706. In some embodiments, the spring 732 can compress if, for example, the upper jaw member 704 contacts a thicker tissue when closing.

Figure 11A:
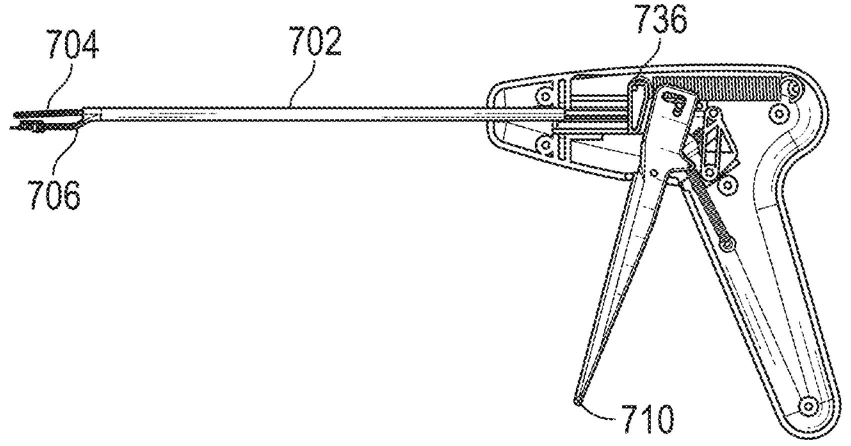
FIGS. 11A-11B show cross-sectional views of a suture passer in a closed jaws configuration and the needle beginning to be deployed.
Figure 11B:
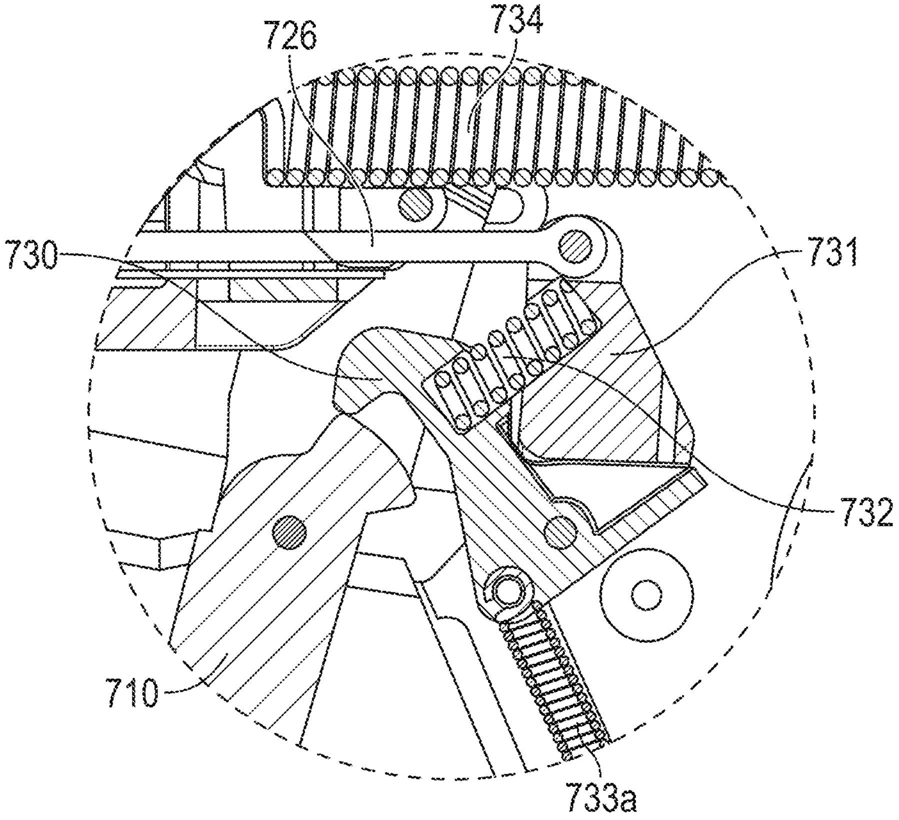

FIGS. 11A-11B illustrate cross-sectional views of a suture passer 700 with the upper jaw member 704 and lower jaw member 706 in a closed configuration and the needle 712 beginning to be deployed. As illustrated in FIG. 11A, the trigger 710 can include a hole that can move around the needle termination 736. Actuating the trigger 710 can cause the needle termination 736 to move (e.g., distally) as the proximal end of the hole in the trigger 710 can push the needle termination 736 forward (e.g., distally). Therefore, partially actuating the trigger 710 can cause the jaw members 704, 706 to close without causing the needle 712 to protrude. As the trigger 710 moves from partially actuated to fully actuated, the proximal end of the hole in the trigger 710 can push the needle termination 736 forward (e.g., distally) to cause the needle 712 to protrude.

Figure 12A:
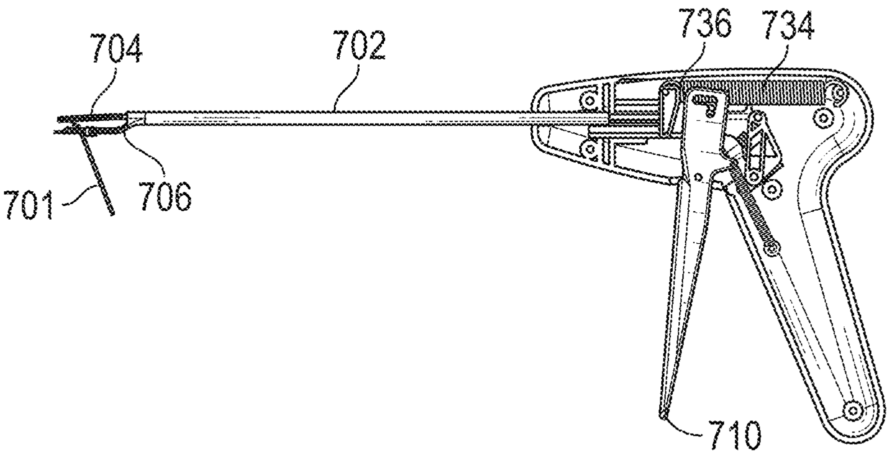
FIGS. 12A-12B show cross-sectional views of a suture passer in a closed jaws configuration with a suture loaded into the suture passer.
Figure 12B:
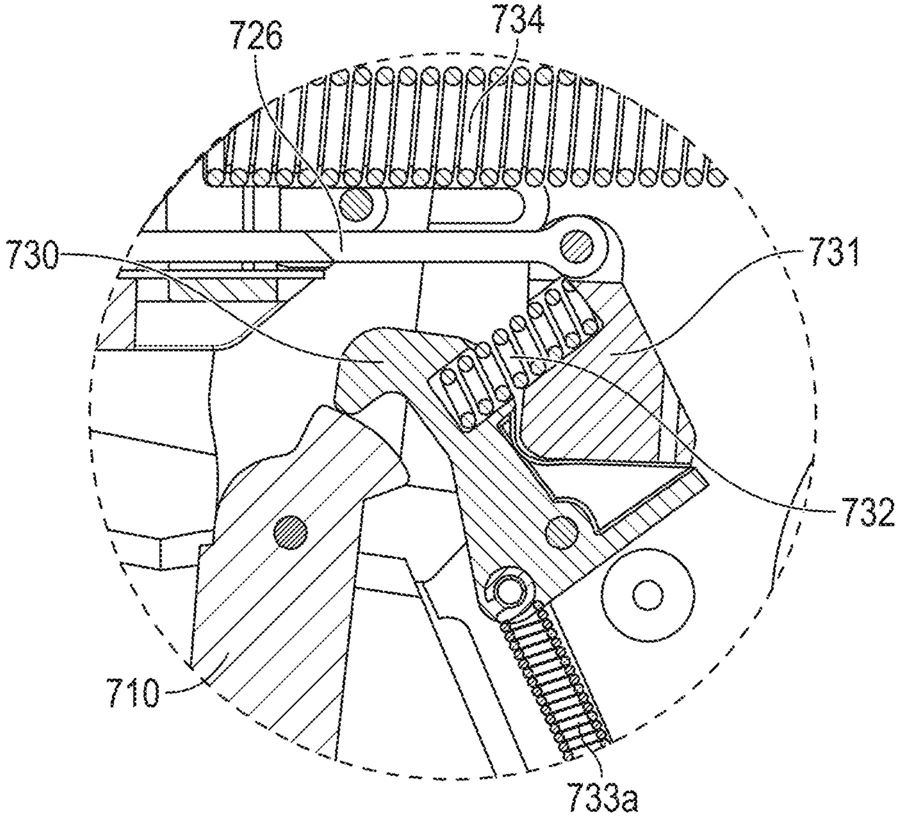

FIGS. 12A-12B illustrate cross-sectional views of a suture passer 700 with the upper jaw member 704 and lower jaw member 706 in a closed configuration with a suture 701 loaded into the suture passer 700.

Figure 13A:
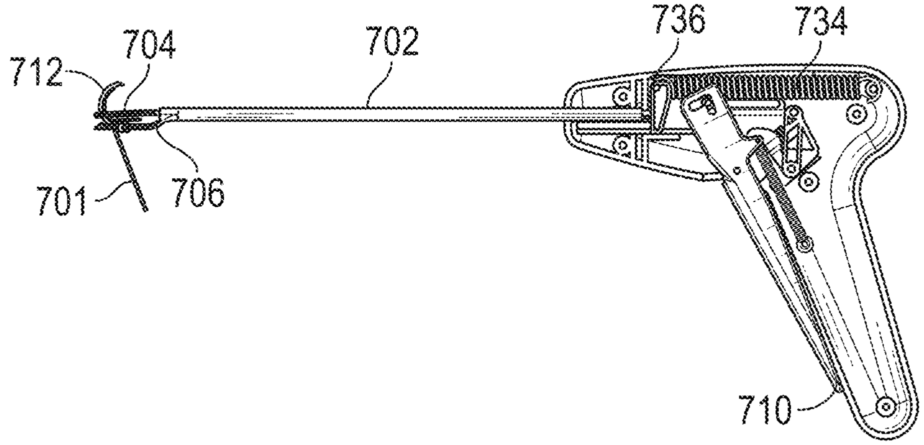
FIGS. 13A-13B show cross-sectional views of a suture passer in a closed jaws configuration and a needle deployed configuration.
Figure 13B:
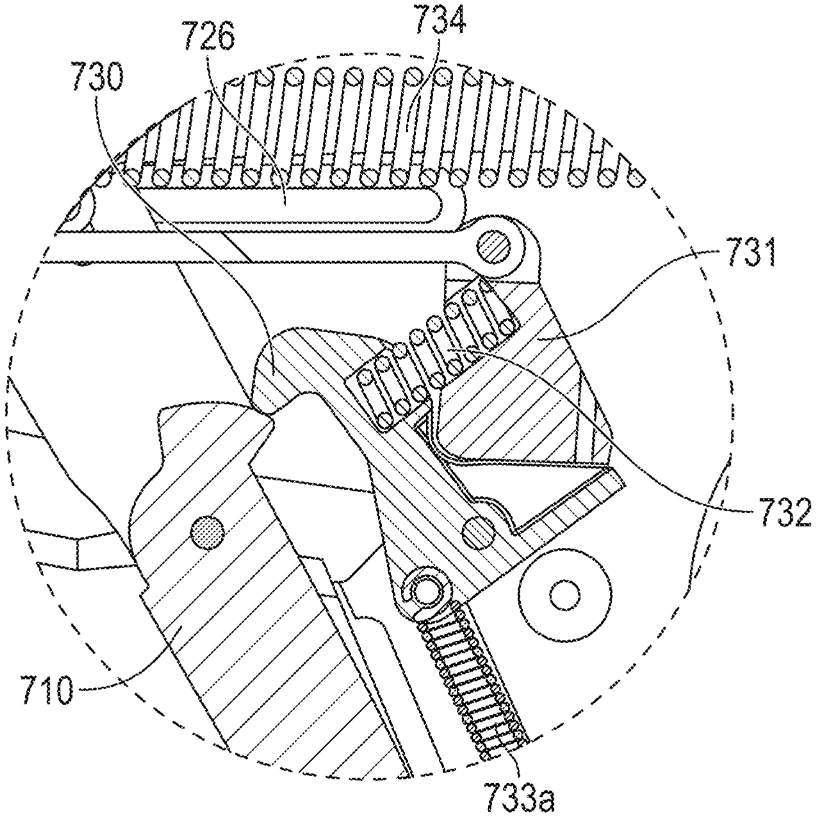

FIGS. 13A-13B illustrate cross-sectional views of a suture passer 700 with the upper jaw member 704 and lower jaw member 706 in a closed configuration and the needle 712 in a deployed configuration. Fully or nearly fully actuating the trigger 710 can cause the needle 712 to protrude from the lower jaw member 706. The trigger 710 can be a two-stage trigger. The first stage of the trigger 710 can include closing the jaw members 704, 706. The second stage of the trigger 710 can include protruding the needle 712 from the lower jaw member 706. In some embodiments, the needle 712 can protrude from the lower jaw member 706 and through the upper jaw member 704. As illustrated in FIG. 13B, the trigger 710 can include a protrusion that only causes the cam 730 to rotate (e.g., relative to the handle 708) when the trigger 710 moves from an unactuated configuration (e.g., the jaws 704, 706 are open) to a partially actuated configuration (e.g., the jaws 704, 706 are closed but the needle 712 is not yet deployed). The protrusion on the trigger 710 may be shaped to maintain the cam 730 in its rotated position, without further rotating the cam 730, when the trigger 710 moves from a partially actuated configuration to a fully actuated configuration (e.g., the jaws 704, 706 are closed and the needle 712 is fully deployed). The trigger 710 may no longer cause the cam 730 to rotate when the trigger 710 moves from partially actuated to fully actuated, which may allow the needle 712 to be deployed without causing one or both of the jaws 704, 706 to continue moving relative to each other.

Figure 14A:
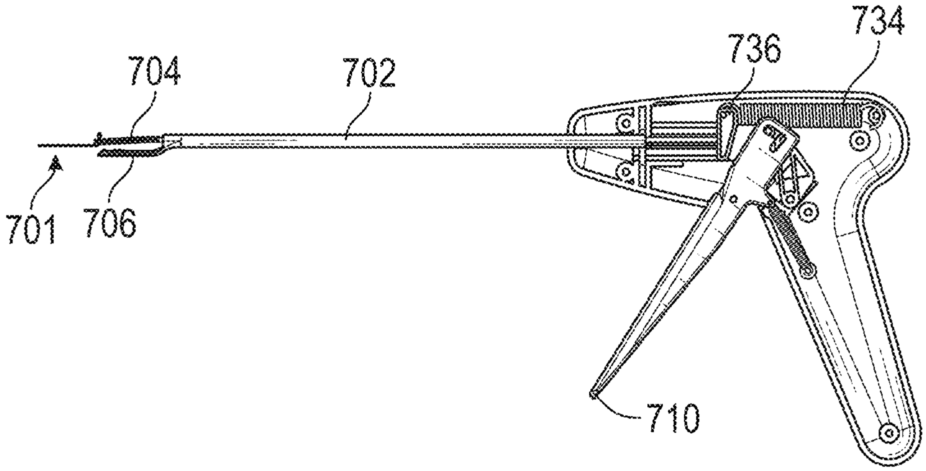
FIGS. 14A-14B show cross-sectional views of a suture passer in a closed jaws configuration and a needle undeployed configuration.
Figure 14B:
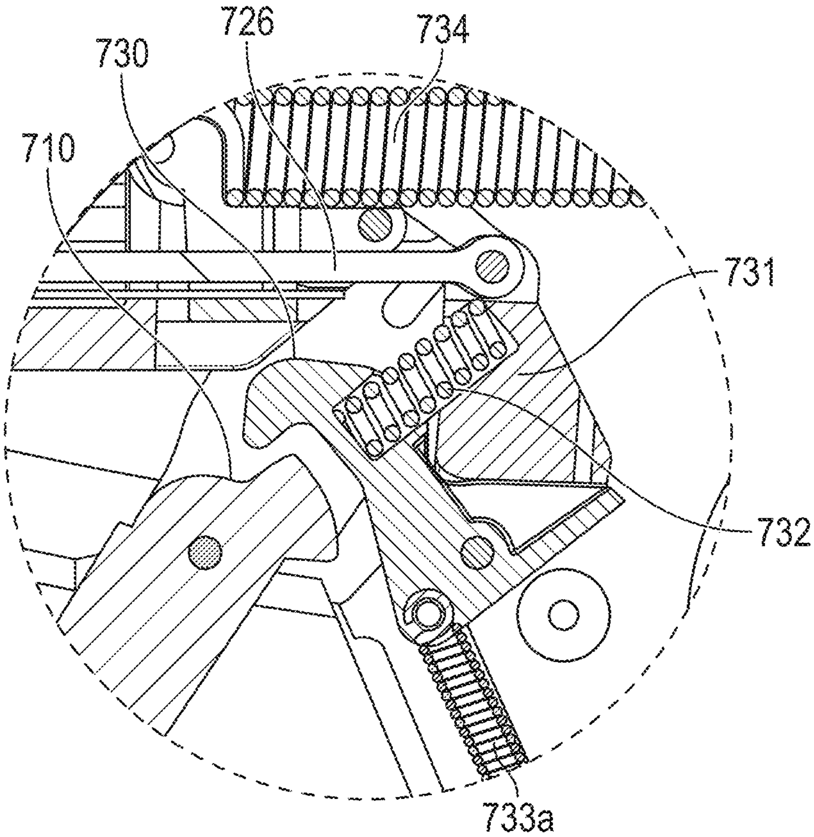

FIGS. 14A-14B illustrate cross-sectional views of a suture passer 700 with the upper jaw member 704 and lower jaw member 706 in a closed configuration and the needle 712 in an undeployed configuration. As illustrated in FIG.

14B, in some embodiments, the closing cam 730 can lift off from the trigger 710, which may cause the jaws 704, 706 to remain in a closed configuration even after the trigger 710 is released. In some embodiments, the closing cam 730 may lift off from the trigger 710 due at least in part to tension in the suture 701. For example, tension in the suture 701, which can be coupled to the needle 712, can cause tension in the closing link 726, which can cause tension in the spring 732, which can cause the closing cam 730 to lift off from the trigger 710. If the tension in the suture 701 is released, then the closing cam 730 may return to its original position on the trigger 710, which may cause the jaws 704, 706 to return to an open configuration.

Figures 15A, 15B:
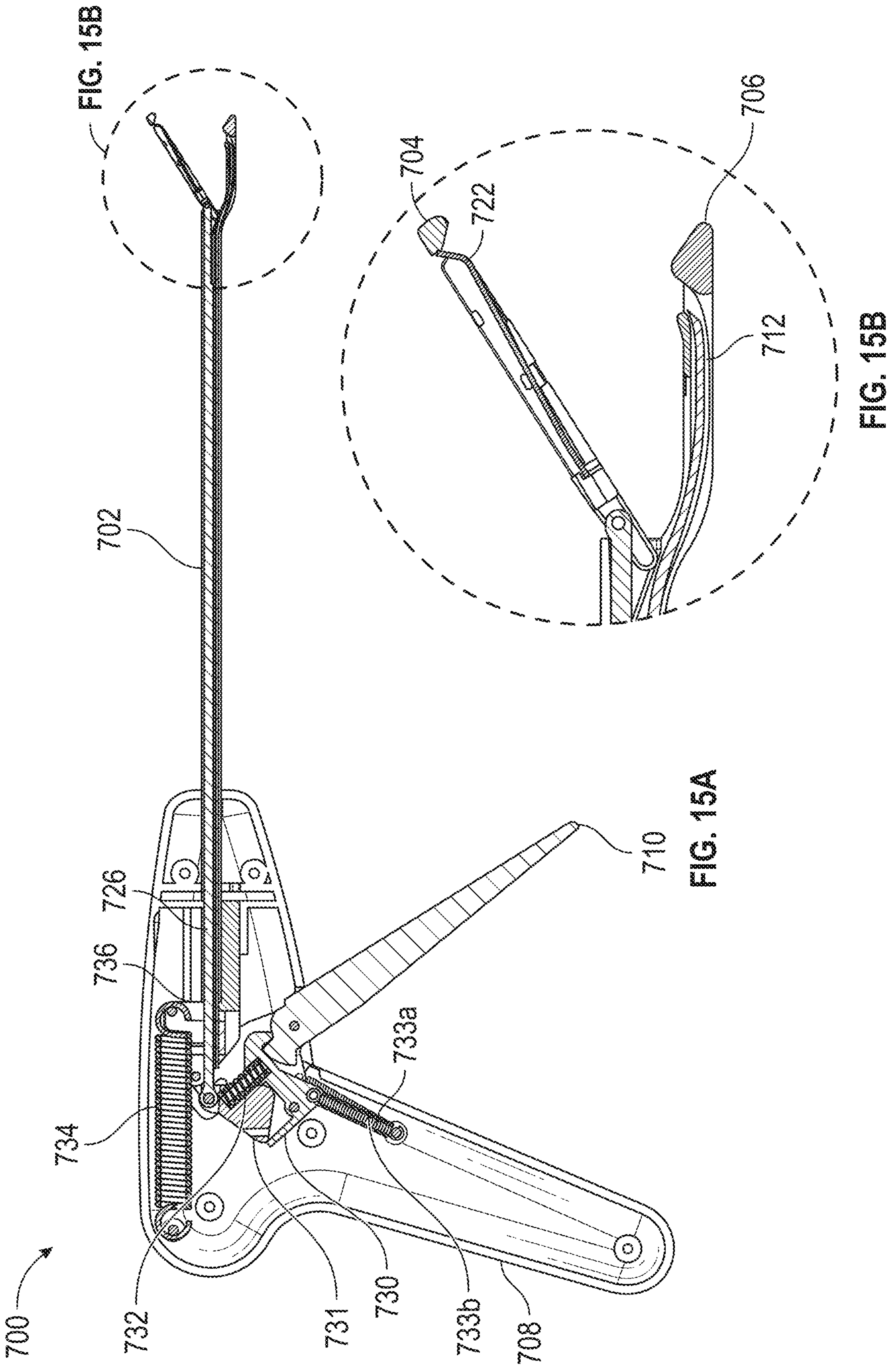
FIGS. 15A-15B show cross-sectional views of a suture passer in an open jaws configuration and a needle undeployed configuration.
Figures 16A, 16B:
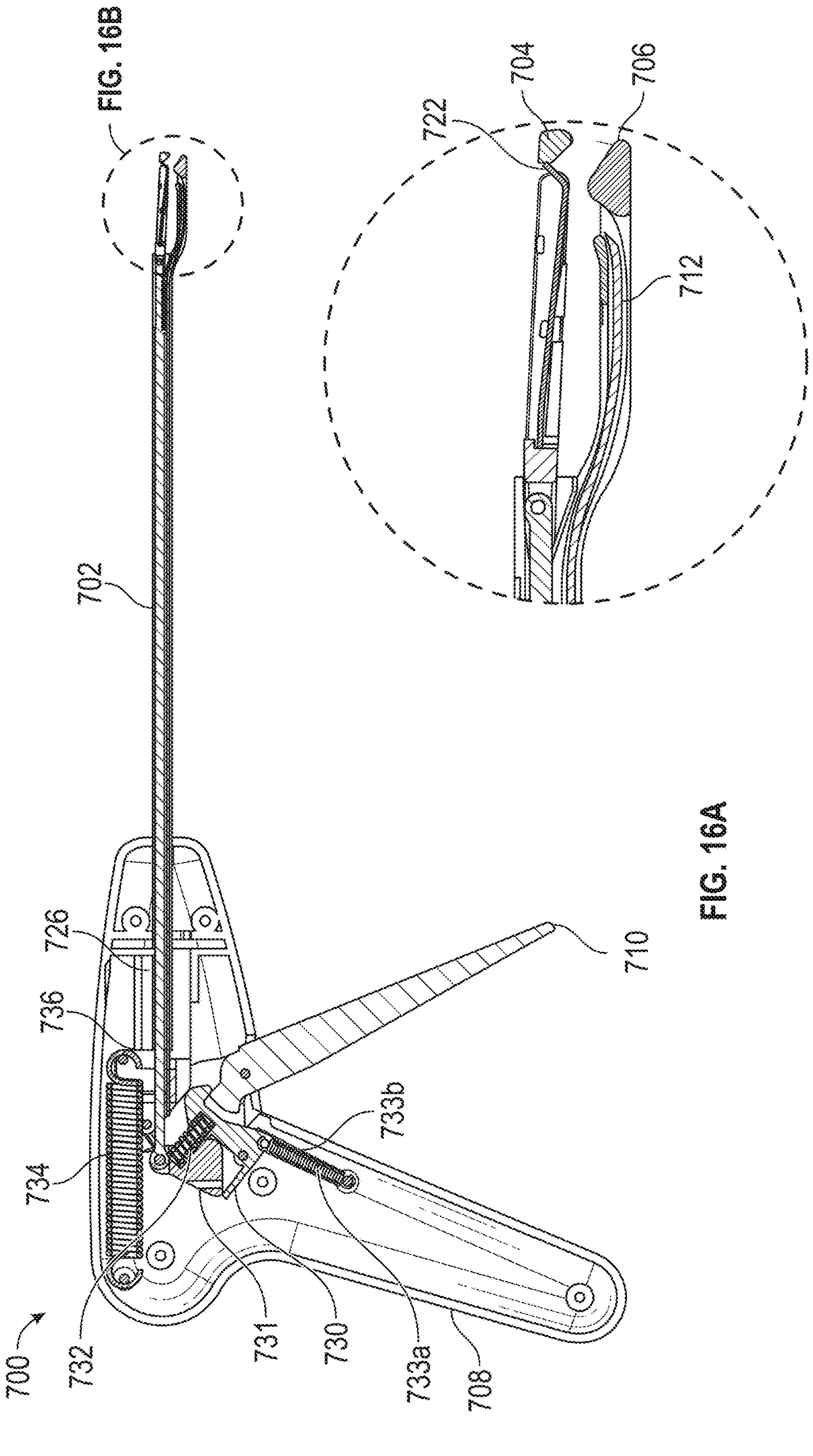
FIGS. 16A-16B show cross-sectional views of a suture passer in a closed jaws configuration and a needle undeployed configuration.
Figure 17A:
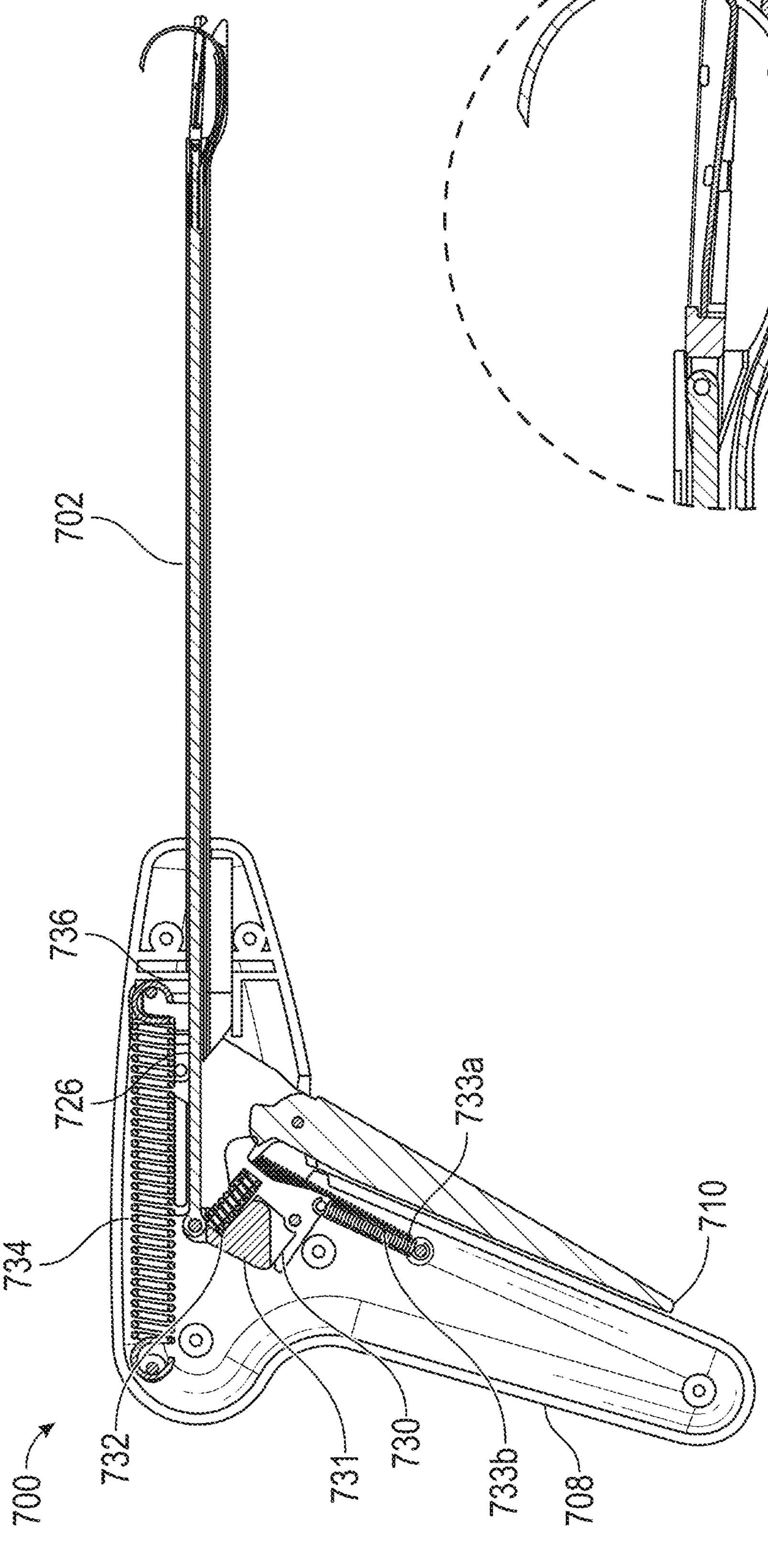
FIGS. 17A-17B show cross-sectional views of a suture passer in a closed jaws configuration and a needle undeployed configuration.
Figure 17B:
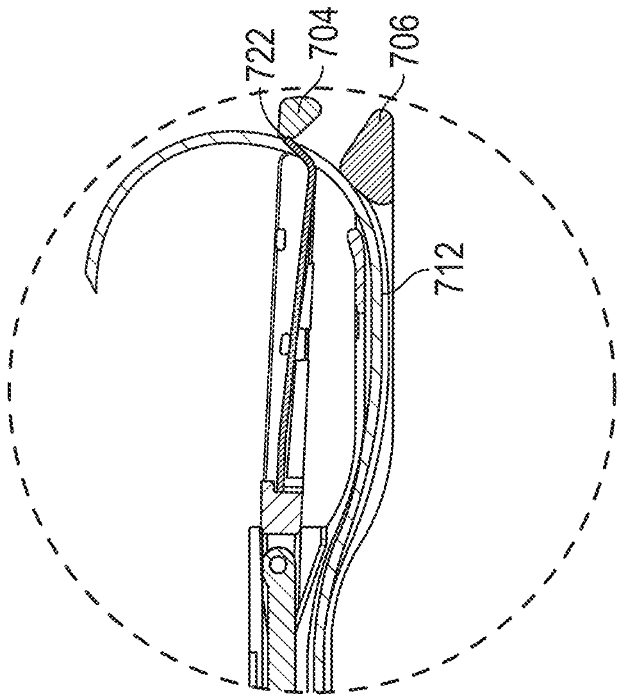

FIGS. 15A-17B illustrate another cross-sectional view of a suture passer 700 with the jaws 704, 706 moving from an open configuration to a closed configuration and the needle 712 moving from an undeployed configuration to a deployed configuration. FIGS. 15A, 16A, and 17A illustrate cross-sectional views of the suture passer 700, and FIGS. 15B, 16B, and 17B illustrate cross-sectional views of the jaws 704, 706 and needle 712, among other things.

FIGS. 15A-14B illustrate cross-sectional views of a suture passer 700 with the upper jaw member 704 and lower jaw member 706 in an open configuration and the needle 712 in an undeployed configuration. The needle 712 can be positioned within the lower jaw member 706. The upper jaw member 704 can extend at an angle relative to the lower jaw member 706 of 45 degrees or approximately 45 degrees, or in a range from 30 degrees or approximately 30 degrees to 60 degrees or approximately 60 degrees, or from 0 degrees or approximately 0 degrees to 90 degrees or approximately 90 degrees, or any value, approximate value, or range of values in the foregoing ranges.

FIGS. 16A-16B illustrate cross-sectional views of a suture passer 700 with the upper jaw member 704 and the lower jaw member 706 in a closed configuration and the needle 712 in an undeployed configuration. The needle 712 can remain in the lower jaw member 706. The upper jaw member 704 can be positioned parallel or substantially parallel with the lower jaw member 706 and/or the elongate member 702. In some embodiments, the upper jaw member 704 can be colinear with the elongate member 702 in a closed configuration.

FIGS. 17A-17B illustrate cross-sectional views of a suture passer 700 with the upper jaw member 704 and the lower jaw member 706 in a closed configuration and the needle 712 in an undeployed configuration. In some embodiments, the needle 712 can extend up (e.g., away from the lower jaw member 706) and out of the lower jaw member 706, and can curve backwards (e.g., proximally) towards the handle. In some embodiments, the needle 712 can curve downwards towards the lower jaw member 706.

Figure 18A:
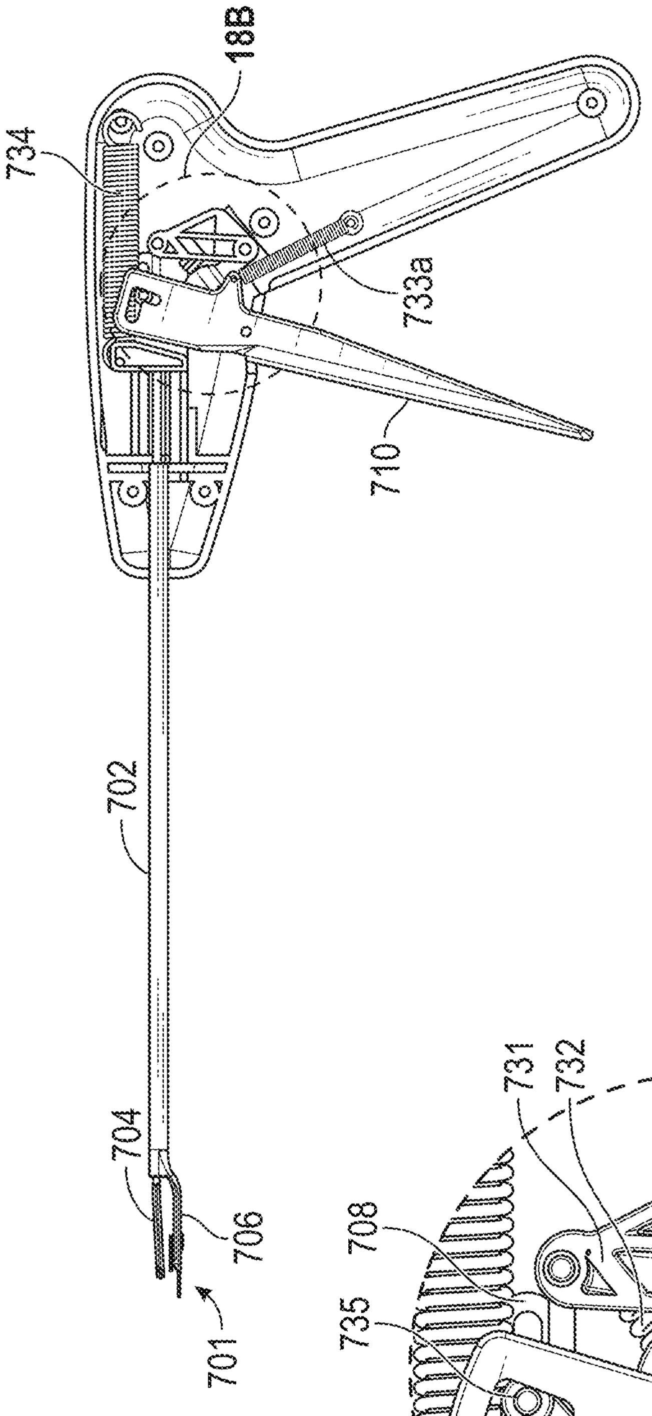
FIGS. 18A-18B show cross-sectional views of a suture passer in a closed jaws configuration and a needle undeployed configuration.
Figure 18B:
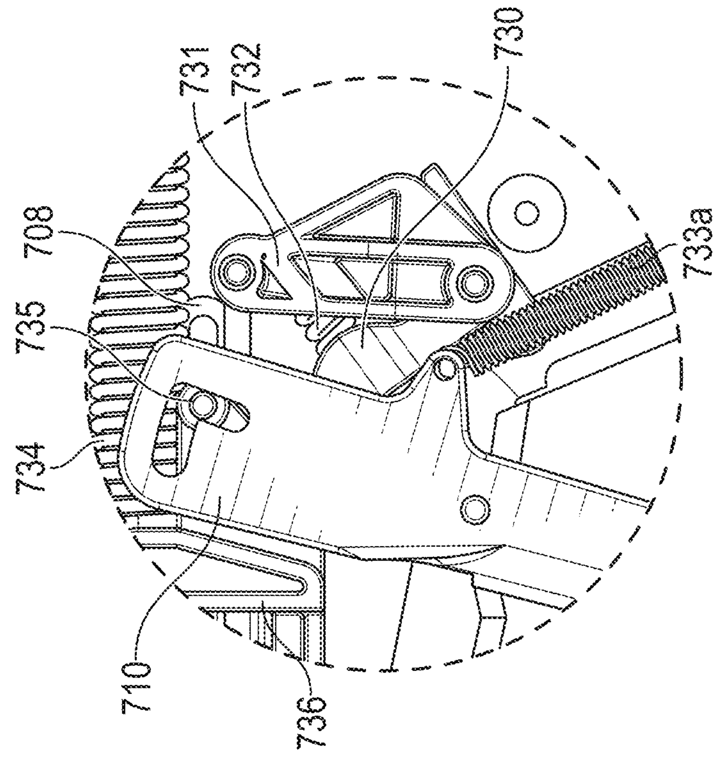
Figure 19A:
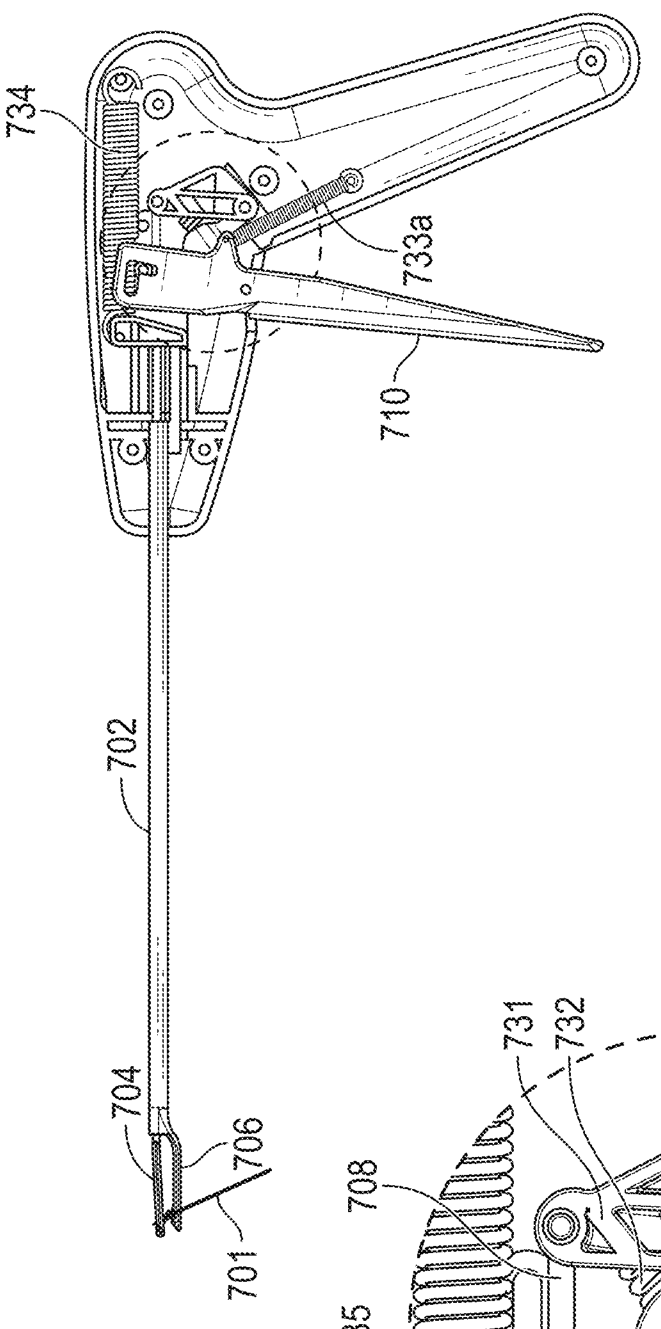
FIGS. 19A-19B show cross-sectional views of suture passer with a needle partially deployed.
Figure 19B:
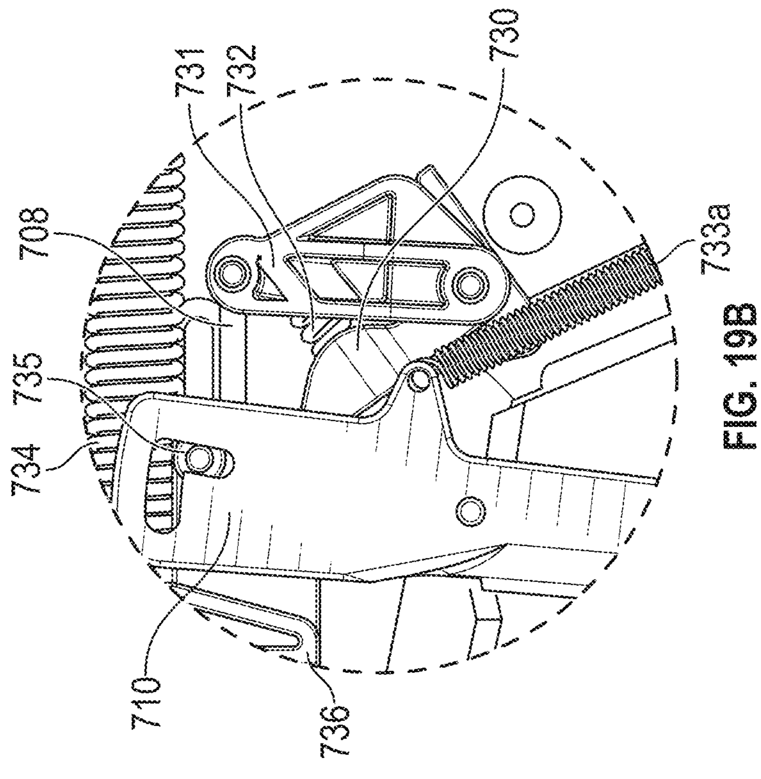
Figure 20A:
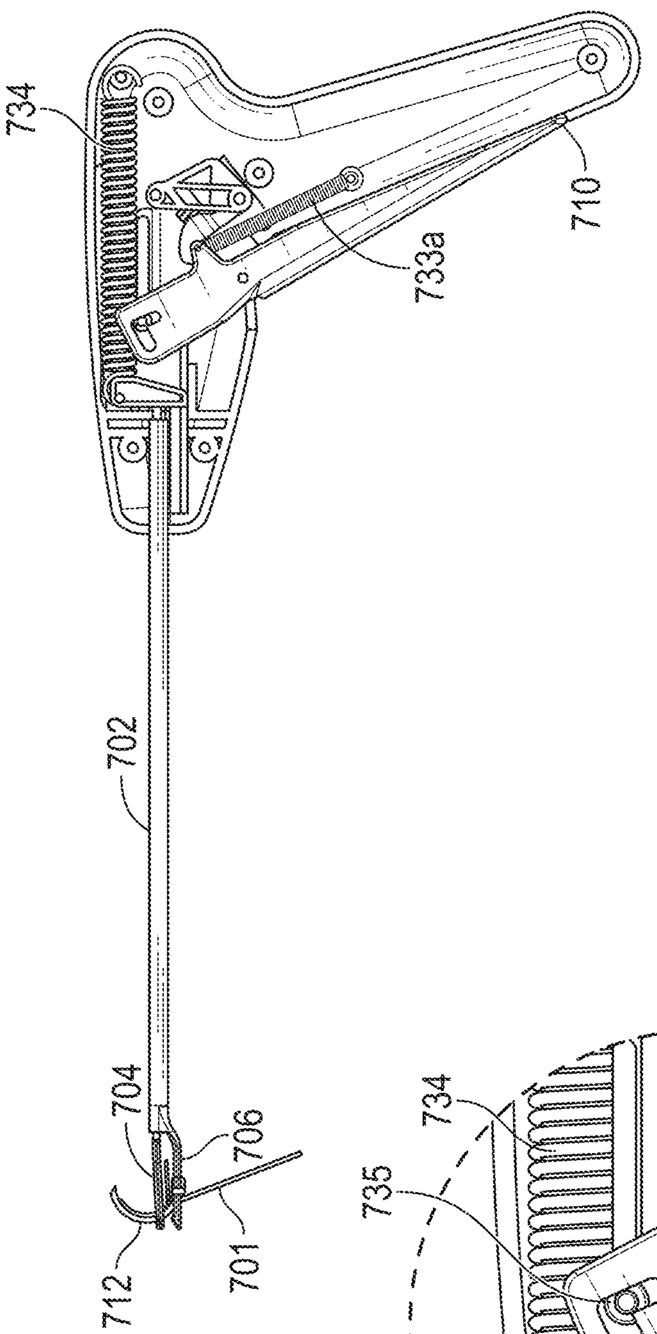
FIGS. 20A-20B show cross-sectional views of a suture passer with a needle in a deployed configuration.
Figure 20B:
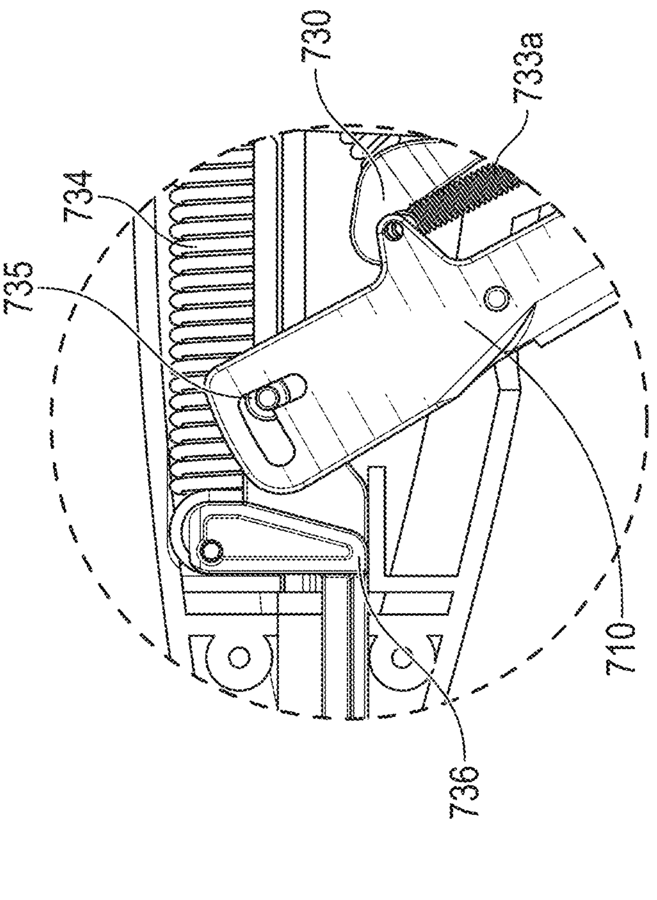

FIGS. 18A-20B illustrate a cross-sectional view of a suture passer 700 with the jaws 704, 706 in a closed configuration and the needle 712 moving from an undeployed configuration to a deployed configuration. FIGS. 18A, 19A, and 20A illustrate cross-sectional views of the suture passer 700, and FIGS. 18B, 19B, and 20B illustrate cross-sectional views of the trigger 110 interacting with the needle termination 736, among other things.

FIGS. 18A-18B illustrate cross-sectional views of a suture passer 700 with the jaws 704, 706 in a closed configuration and the needle in an undeployed configuration. A pin 735 can be coupled to the needle termination 736 and can slide through a slot in the handle 708 and a hole in the trigger 710. As the trigger 710 (e.g., is actuated), the hole in the trigger 710 can move such that the proximal end of the hole encounters the pin 735. As the trigger 710 continues to the actuated, the proximal end of the hole can push the pin 735 along the slot in the handle 708. The slot can be an elongated slot, elongated in the distal direction. Since the pin 735 can be coupled to the needle termination 736, movement of the pin distally along the slot can cause the needle termination to move distally, which may cause the needle 712 to extend from the lower jaw member 706.

FIGS. 19A-19B illustrate cross-sectional views of suture passer 700 with the needle 712 partially deployed. As compared to FIGS. 18A-18B, the pin 735 and the needle termination 736 can move distally towards the distal end of the elongate member 702.

FIGS. 20A-20B illustrate cross-sectional views of a suture passer 700 with the needle 712 in a deployed configuration. As compared to FIGS. 18A-19B, the pin 735 and the needle termination 736 can move distally towards the distal end of the elongate member 702. The extension springs 733*a*, 733*b* can be biased such that release of the trigger 710 can allow the springs 733*a*, 733*b* to move the trigger 110 back into an unactuated configuration. The spring 734 can be biased such that release of the trigger 710 can allow the spring 734 to cause the needle termination 736 to move backwards (e.g., proximally) to its original position (e.g., an undeployed configuration).

Figure 21:
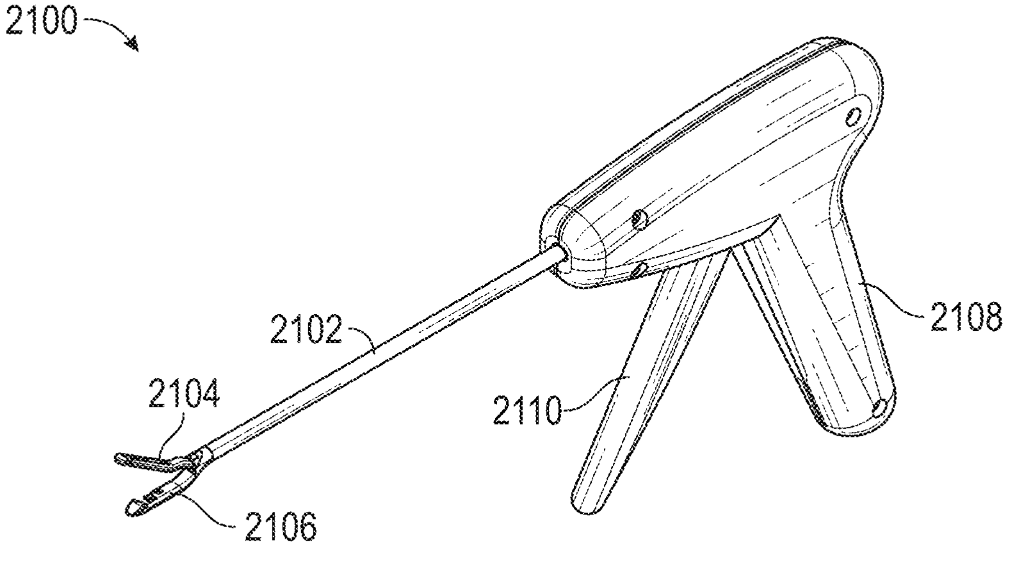
FIG. 21 shows an example embodiment of a suture passer.

FIG. 21 illustrates another embodiment of a suture passer 2100. The suture passer 2100 can be similar to the suture passer 100 of FIGS. 1A-1B, 2A-C, 3A-C, and 4A-C, suture passer 500 of FIG. 5, suture passer 600 of FIGS. 6A-C, and/or suture passer 700 of FIGS. 7-20B and can have any of the same or similar elements, components, or features. The suture passer 100 of FIGS. 1A-1B, 2A-C, 3A-C, and 4A-C, suture passer 500 of FIG. 5, suture passer 600 of FIGS. 6A-C and/or suture passer 700 of FIGS. 7-20B can be similar to suture passer 2100 and can have any of the same or similar elements, components, or features. In some examples, with respect to FIGS. 21-25, the suture passer can include a "Y" shaped closing cam, or a closing cam with three linear projections from a center point, instead of the three components that make up the cam in examples illustrated in FIGS. 7-20. The closing cam can be configured to flex if thick tissue is encountered. Additionally, liftoff of the closing cam can be eliminated so that an end user can force the jaws open. In some examples, the cam surface on the trigger can be replaced with a cam slot, such as the cam slot used to advance the needle.

Figure 22:
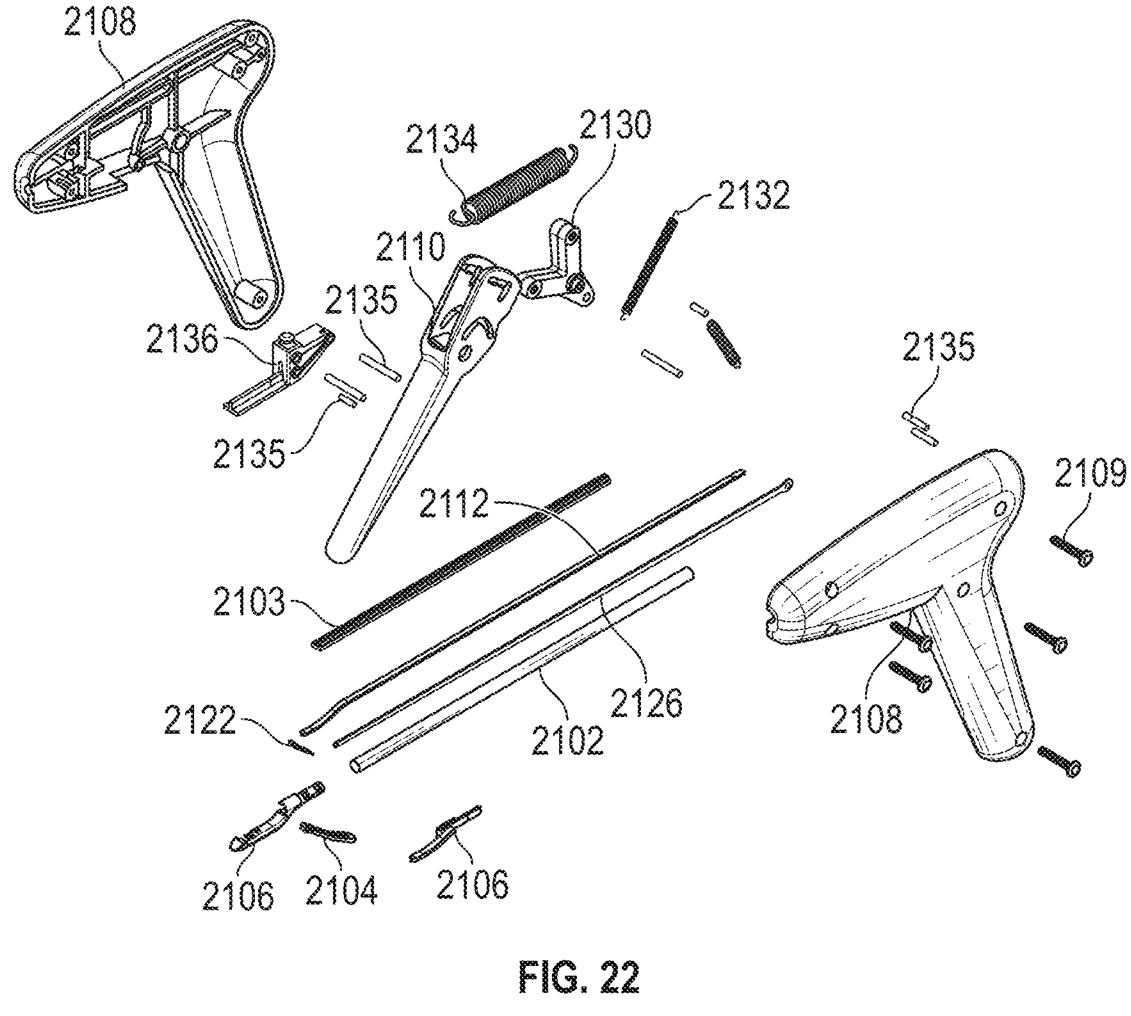
FIG. 22 show an exploded view of the suture passer of FIG. 21.

FIG. 22 illustrates an exploded view of a suture passer 2100. The suture passer 2100 can include, for example, a handle 2108, a trigger 2110, an elongate member 2102, an upper jaw member 2104, a lower jaw member 2106, a needle 2112, a needle termination 2136, and a closing link 2126. The suture passer 2100 can include a shaft insert 2103, which can be positioned within the elongate member 2102 and can help guide the needle termination 2136 as the needle termination moves distally and proximally within the handle 2108. The suture passer 2100 can include a closing cam 2130 and an extension spring 2132 which can engage with the trigger 2110 and the closing link 2126 to cause the jaws 2104, 2106 to open and close. The suture passer 2100 can include pins 2135 and/or screws 2109 that can couple various components within the handle 2108. The suture passer 2100 can include spring 2134 which can couple the needle termination 2136 to the handle 2108. A suture retainer 2122 can grab or retain the suture through the upper jaw 2104.

FIGS. 23A-25B illustrate cross-sectional views of a suture passer 2100 with the upper jaw member 2104 and lower jaw member 2106 moving from an open configuration to a closed configuration and the needle 2112 moving from an undeployed configuration to a deployed configuration.

Figure 23A:
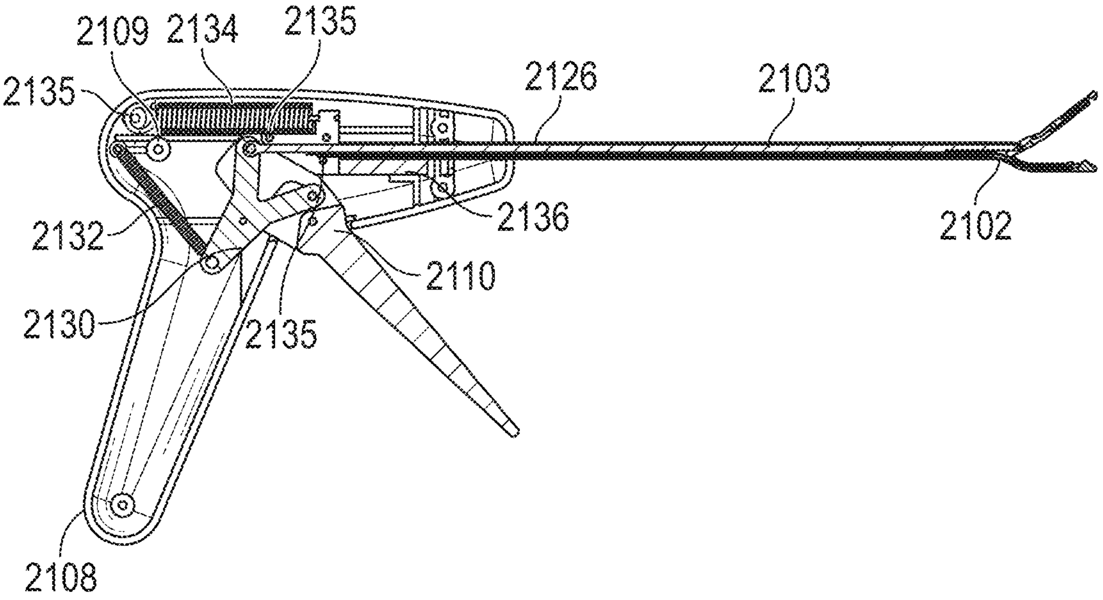
FIGS. 23A-23B cross-sectional views of the suture passer in an open jaws configuration and a needle undeployed configuration.
Figure 23B:
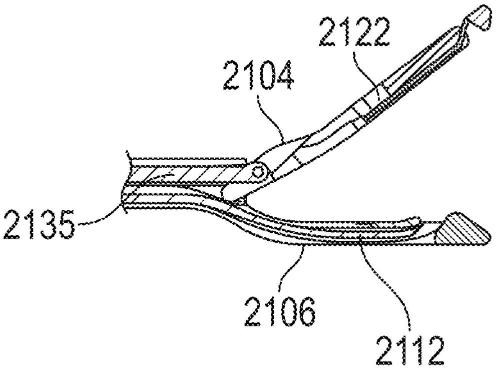

FIGS. 23A-23B illustrate cross-sectional views of the suture passer 2100 with jaws 2104, 2106 in an open configuration and with the needle 2112 in an undeployed configuration. In some embodiments, the closing cam 2130 can have a Y-shape or a triangular shape, where a first portion can be coupled to handle 2108 via an extension spring 2132, a second portion can be coupled to the closing link 2126, and a third portion can be coupled to the trigger 2110 via a pin 2135. In some embodiments, the closing cam 2130 can have another shape. The closing cam 2130 is designed to provide compliance so that in the eventuality the upper jaw contacts tissue before full actuation of the closing cam 2130, the legs of the closing cam 2130 will deflect to allow full actuation.

Figure 24A:
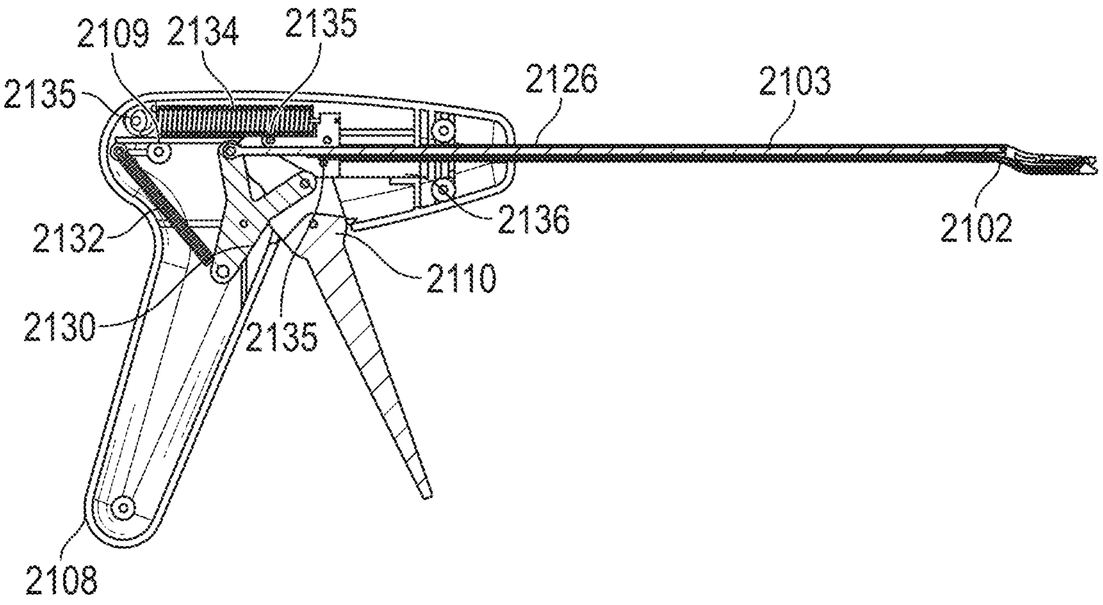
FIGS. 24A-24B show a cross-sectional view of the suture passer in a closed jaws configuration and a needle undeployed configuration.
Figure 24B:
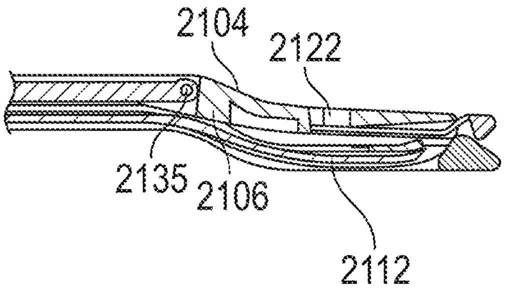

FIGS. 24A-24B illustrate cross-sectional views of the suture passer 2100 with the jaws 2104, 2106 in a closed configuration and with the needle 2112 in an undeployed configuration. Actuating the trigger 2110 can cause rotation (e.g., relative to the handle 2108) of the closing cam 2130, which may cause the closing link 2126 to move, which may cause the upper jaw member 2104 to move towards the lower jaw member 2106.

Figure 25A:
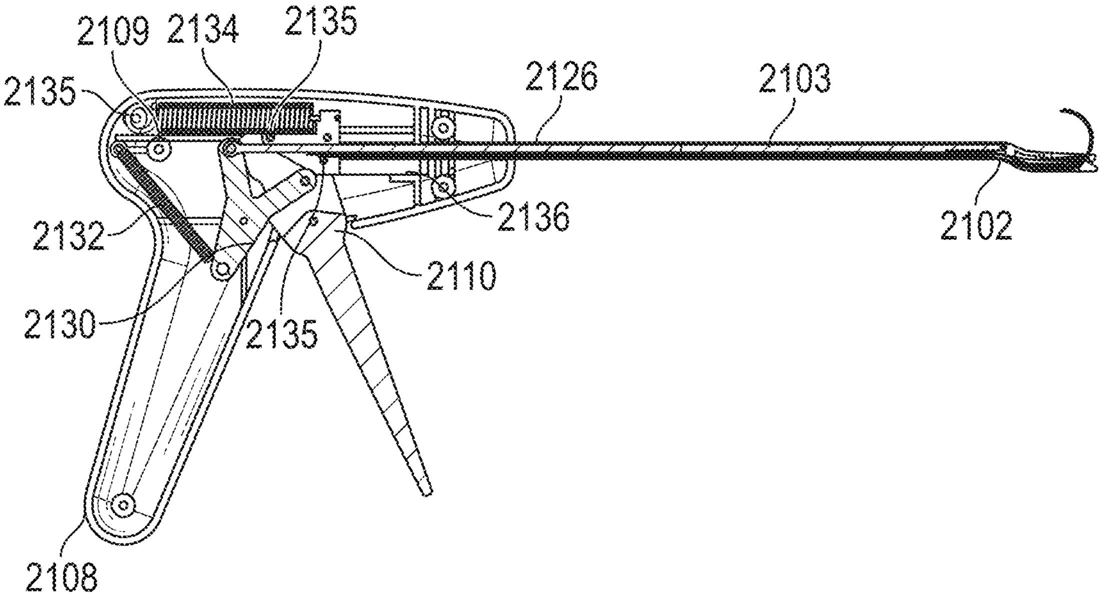
FIGS. 25A-25B cross-sectional views of the suture passer in a closed jaws configuration and a needle deployed configuration.
Figure 25B:
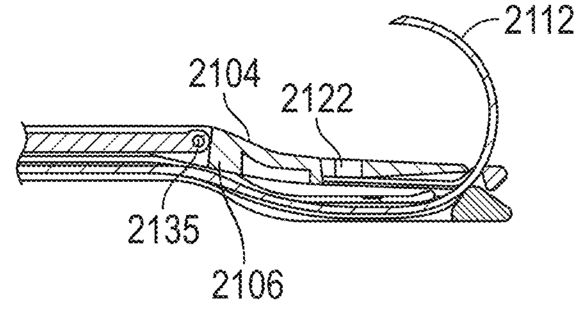

FIGS. 25A-25B illustrate cross-sectional views of the suture passer 2100 with the jaws 2104, 2106 in a closed configuration and the needle 2112 in a deployed configuration. Actuating the trigger 2110 may cause the needle termination 2136 to move distally, which may cause the needle 2112 to extend from the lower jaw member 2106.

FIGS. 26A-33B illustrate a method of loading a suture 2601 on a suture passer (e.g., any of the suture passer embodiments disclosed herein, including without limitation suture passer 100, 500, 600, 700, 2100). In some embodiments, a loop of the suture 2601 can be placed over the jaw member with the needle 2612 (e.g., lower jaw member 2606) while the jaws 2604, 2606 are open. The jaws 2604, 2606 can be closed to retain the suture 2601 in place. The needle 2612 can be partially deployed such that a portion of the needle 2612 captures the suture 2601. As the needle 2612 fully extends, the suture 2601 can be retained on the portion of the needle 2612 proximal to the distal end, passing the suture 2601 through the tissue. The suture retainer 2622 can keep the suture 2601 in position as the needle 2612 is retracted. To unload the suture 2601, the user can pull up on the suture loop that is maintained across the tissue by the suture retainer 2622. In some embodiments, the suture 2601 can be released from the upper jaw member 2604 by pulling up on the short suture end, which can prevent damage, such as fraying, to the suture 2601 that could otherwise occur during intricate unloading of the suture 2601.

Figure 26A:
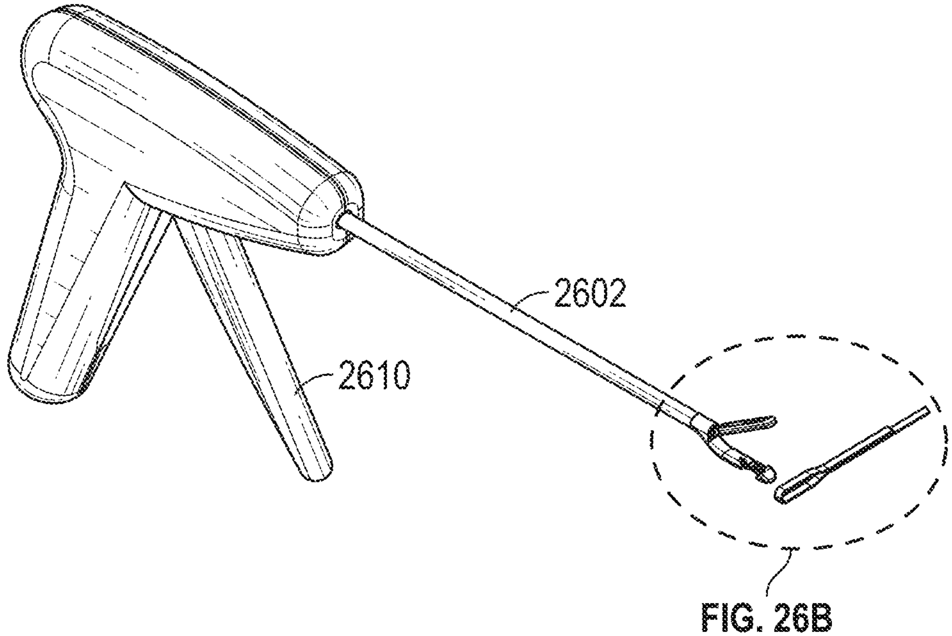
FIGS. 26A-26B show the upper jaw member and lower jaw member of a suture passer and a suture.
Figure 26B:
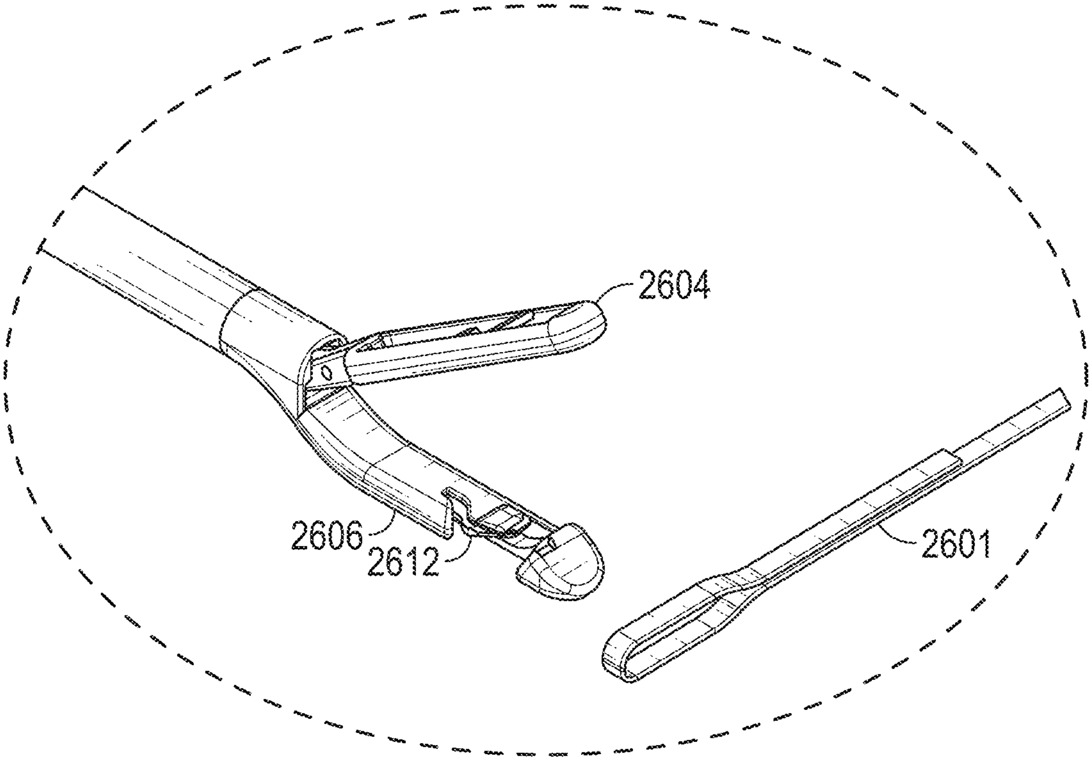

FIGS. 26A-26B illustrate the upper jaw member 2604 and lower jaw member 2606 of a suture passer (e.g., suture passer 100, 500, 600, 700, 2100) and a suture 2601. The suture 2601 can include a loop and can be positioned near the jaws 2604, 2606 when the jaws 2604, 2606 are in an open configuration and the needle 2612 is in an undeployed configuration. A suture passer 2600 can include an elongate member 2602, an upper jaw member 2604, a lower jaw member 2606, a needle 2612, and a trigger 2610.

Figure 27A:
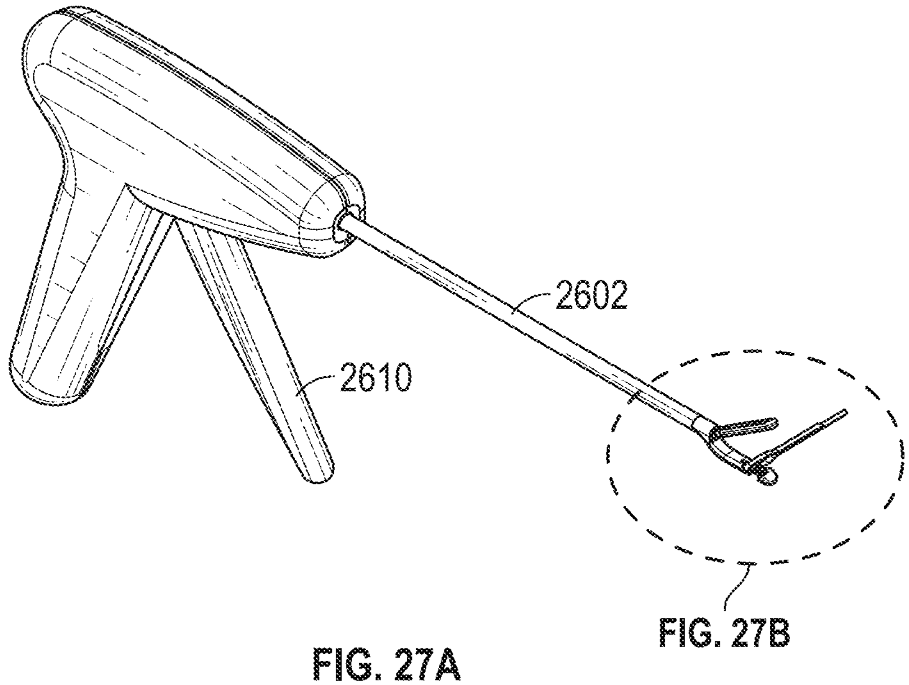
FIGS. 27A-27B show a loop of the suture positioned over the lower jaw member of a suture passer.
Figure 27B:
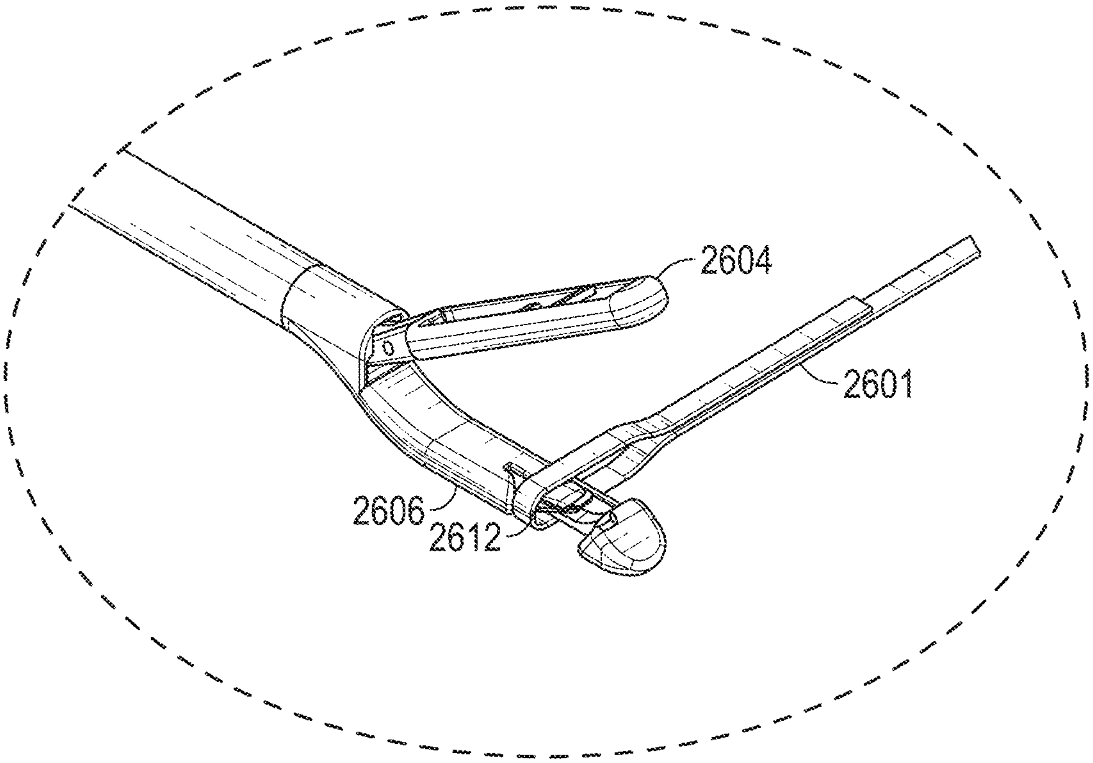

FIGS. 27A-27B illustrate the loop of the suture 2601 positioned over (e.g., around) the lower jaw member 2606. The loop of the suture 2601 can be positioned over the lower jaw member 2606 while the jaws 2604, 2606 remain in an open configuration and the needle 2612 remains in an undeployed configuration. The suture 2601 can be positioned such that the loop is positioned over a distal end (e.g., the sharp end) of the needle 2612.

FIGS. 28A-28C illustrate the suture 2601 positioned within a notch of the needle 112 which can allow the needle 2612 to capture the suture 2601. The lower jaw member 2606 can include a suture loader (e.g., an opening or notch), in which the suture can be positioned or routed, which can allow the suture 2601 to be positioned within the notch of the needle 2612. The notch of the needle 2612 can be aligned with the suture loader of the lower jaw member 2606 when the needle 2612 is in an undeployed configuration. FIG. 28C illustrates a top section view of the suture 2601 positioned within the notch of the needle 2612 and within a notch of the lower jaw member 2606.

Figure 29A:
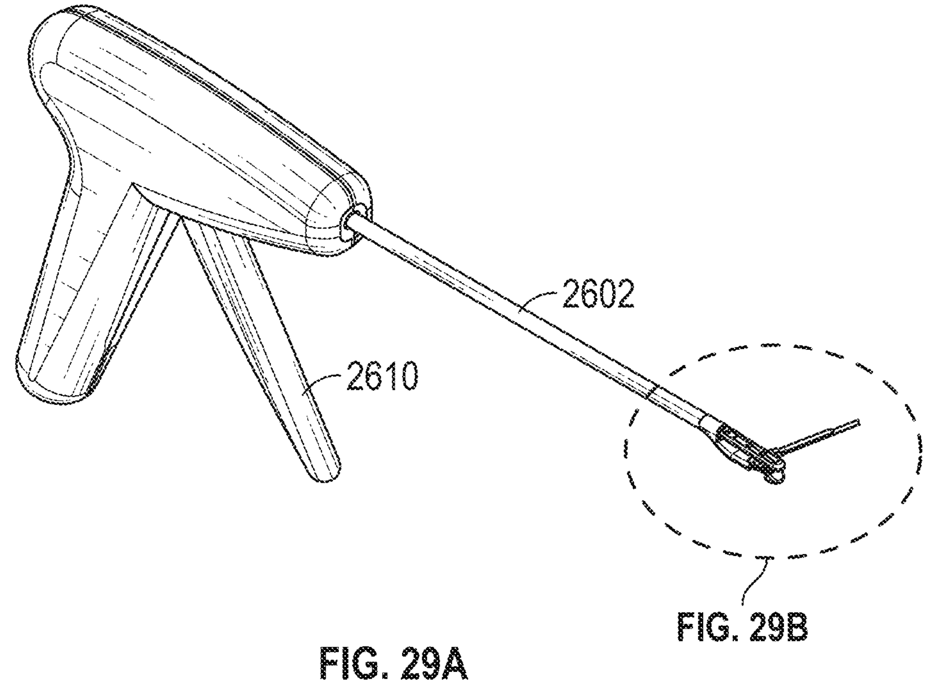
FIGS. 29A-29B show the jaws of a suture passer in a closed jaws configuration.
Figure 29B:
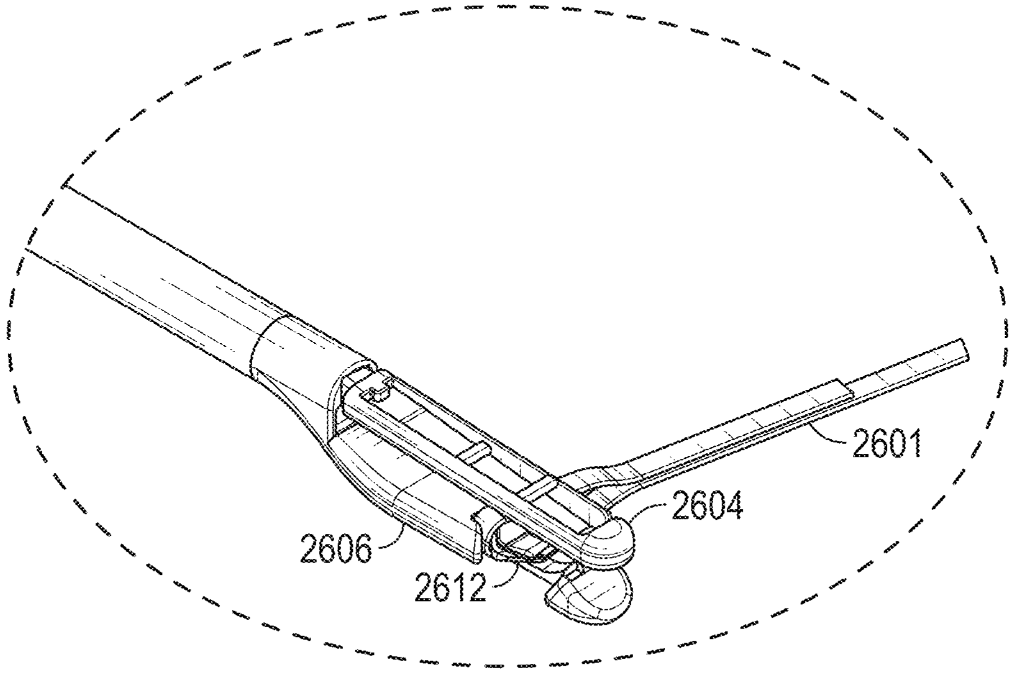

FIGS. 29A-29B illustrate the jaws 2604, 2606 in a closed configuration. Closing the jaws 2604, 2606 can retain the suture 2601 in place when the suture 2601 is positioned within the jaws 2604, 2606 (e.g., over lower jaw member 2606).

Figure 30A:
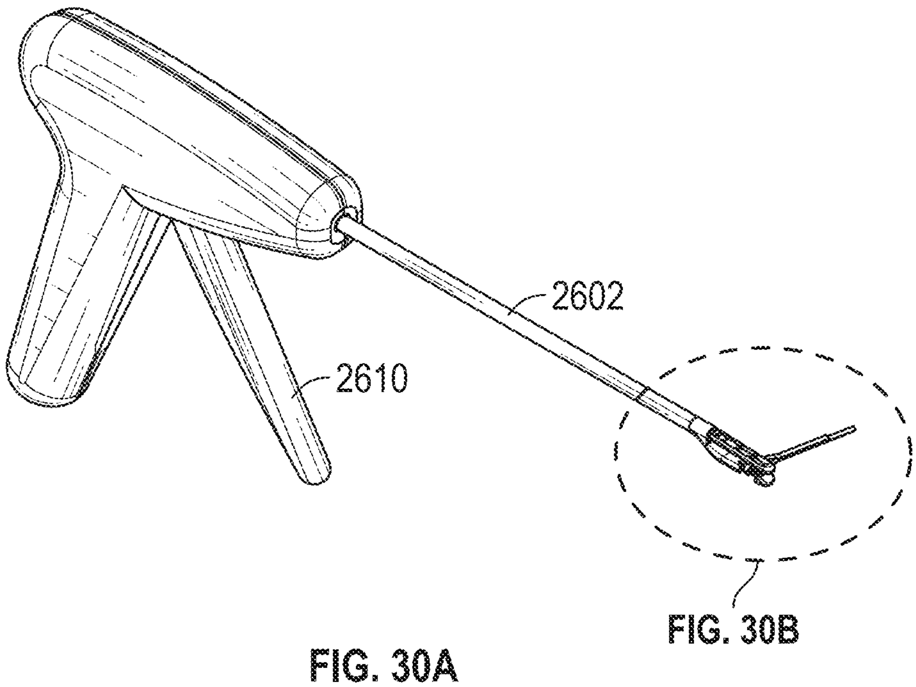
FIGS. 30A-30B show a suture positioned within the upper jaw member and lower jaw member.
Figure 30B:
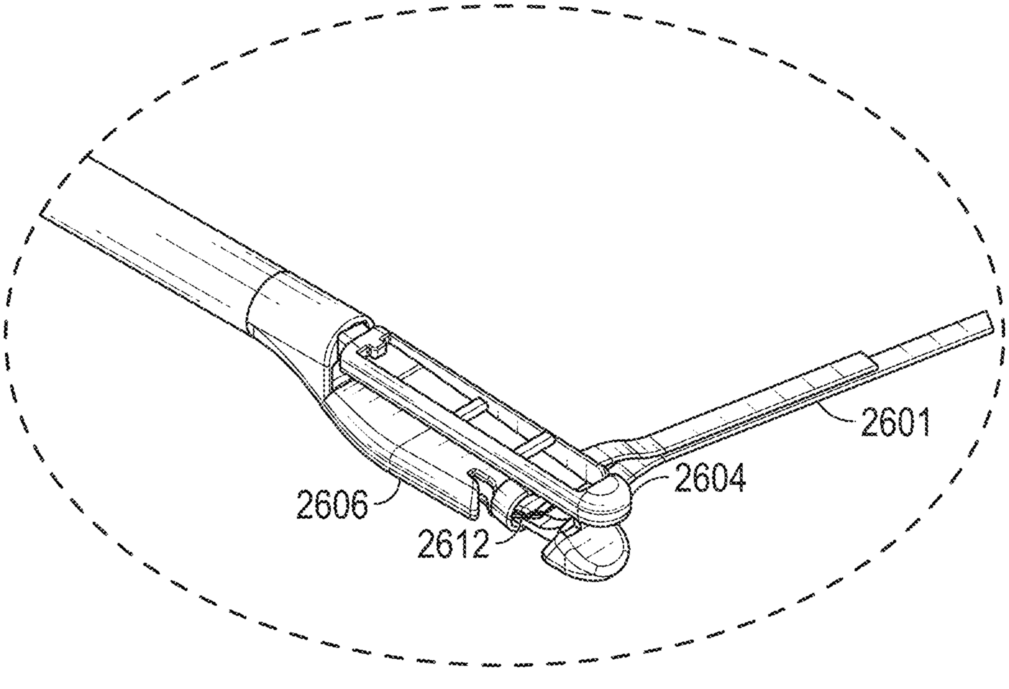

FIGS. 30A-30B illustrate the suture 2601 positioned within the upper jaw member 2604 and lower jaw member 2606. After the loop of the suture 2601 is positioned within the notch of the needle 2612, one or both ends of the suture 2601 can be positioned in preparation for deployment of the needle 2612. For example, one end of the suture 2601 can be moved from one side of the jaws 2604, 2606 to other side, as shown in FIGS. 30B and 31B.

Figure 31A:
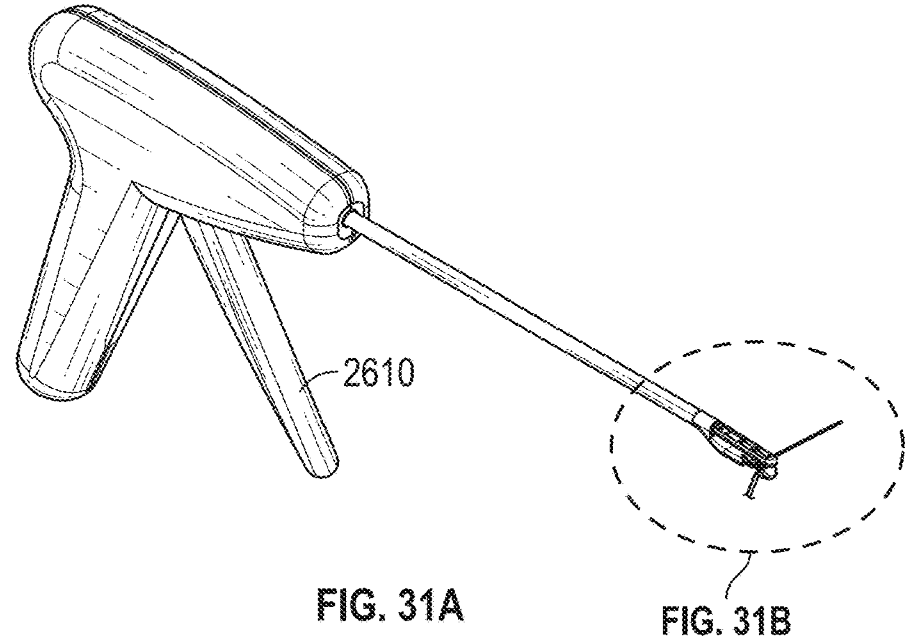
FIGS. 31A-31C show a suture positioned within the jaws with the needle partially deployed.
Figure 31B:
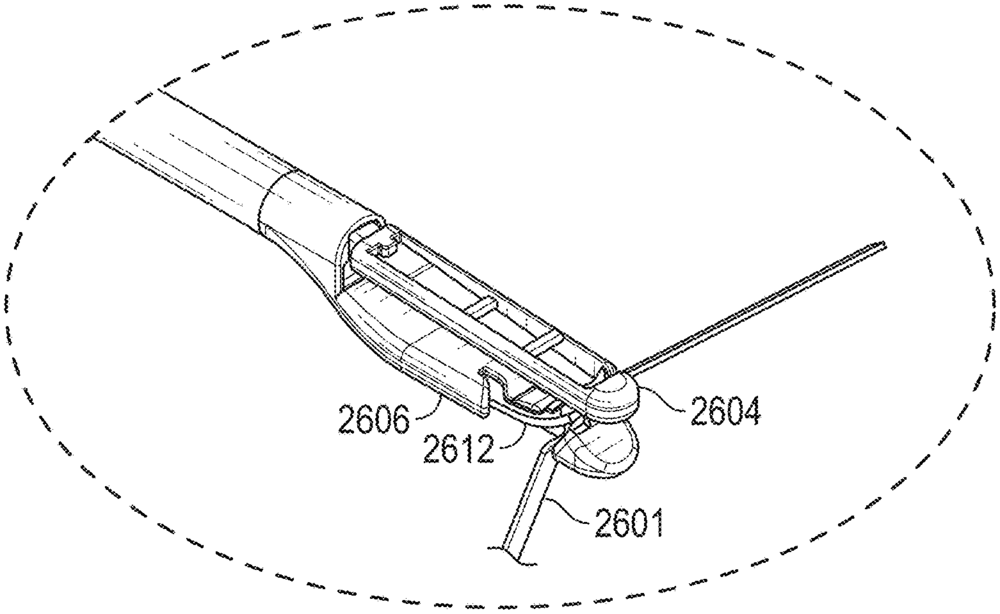
Figure 31C:
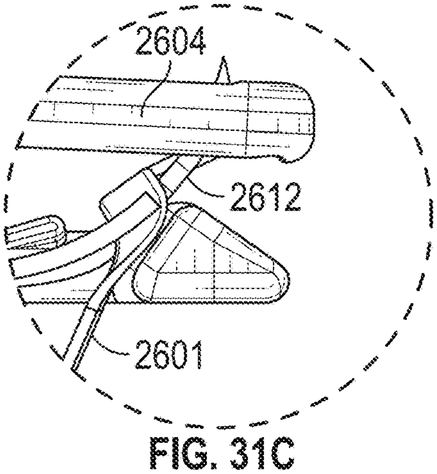

FIGS. 31A-31C illustrate the suture 2601 positioned within the jaws 2604, 2606 with the needle 2612 partially deployed. Deploying or partially deploying the needle 2612 can cause a portion of the needle 2612 (e.g., a notch of the needle 2612) to capture the suture 2601.

Figure 32A:
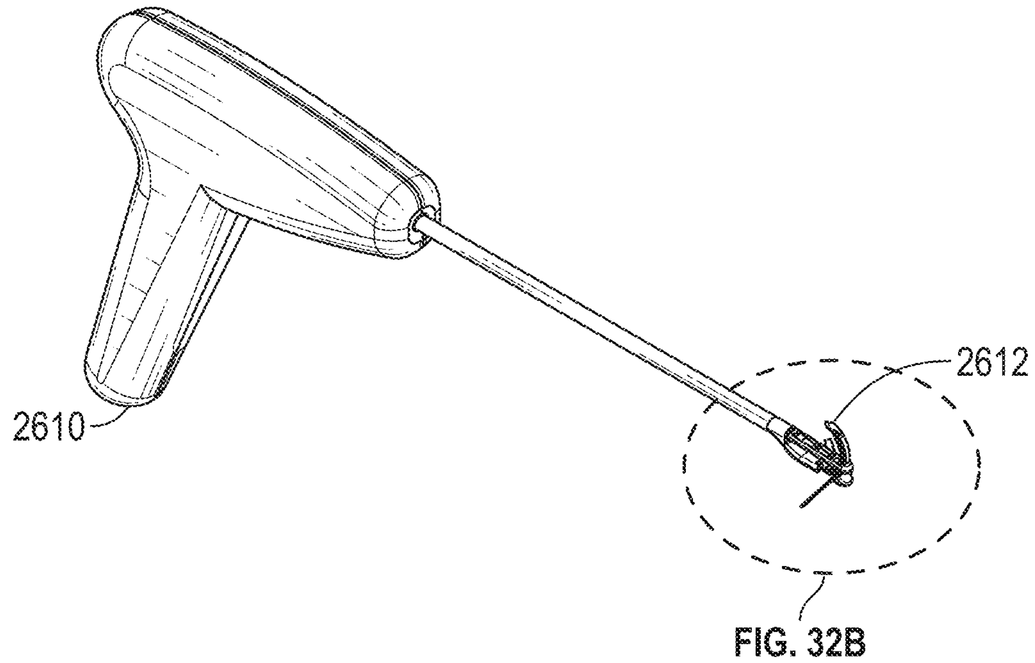
FIGS. 32A-32B show a needle in a deployed configuration.
Figure 32B:
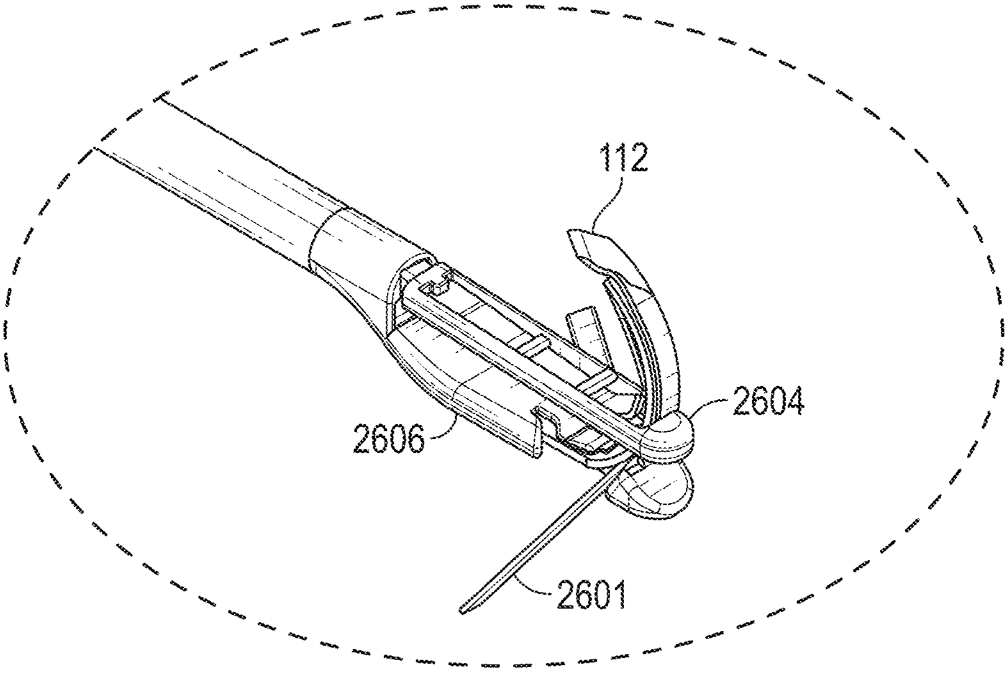

FIGS. 32A-32B illustrate the needle 2612 in a deployed (e.g., extended) configuration. As the needle 2612 extends, the suture 2601 can be retained on the portion of the needle proximal to the distal end (e.g., a notch), which can cause the suture 2601 to be passed through tissue.

Figure 33A:
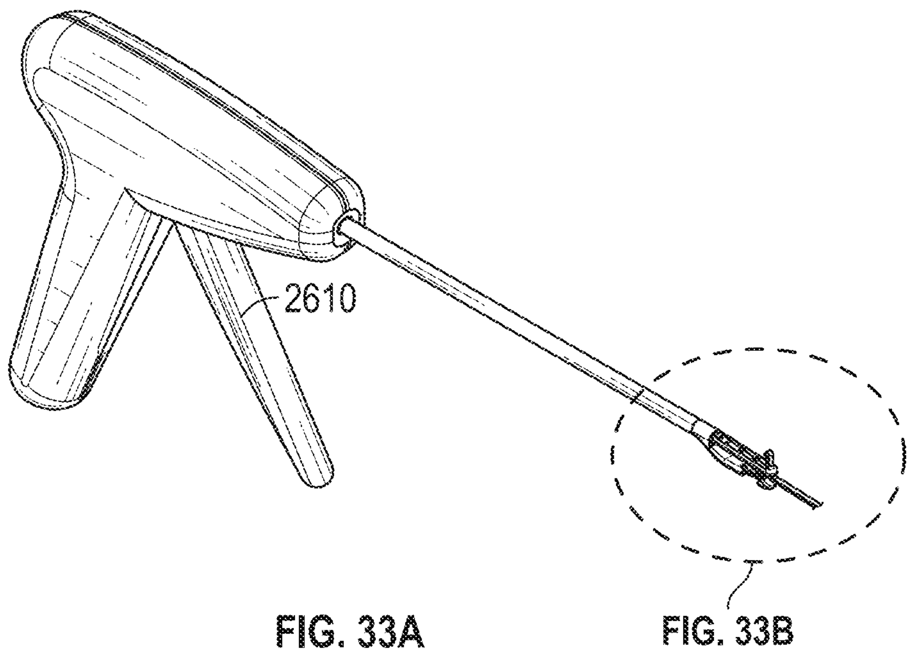
FIGS. 33A-33B show the jaws of a suture passer in a closed configuration with the needle in an undeployed configuration.
Figure 33B:
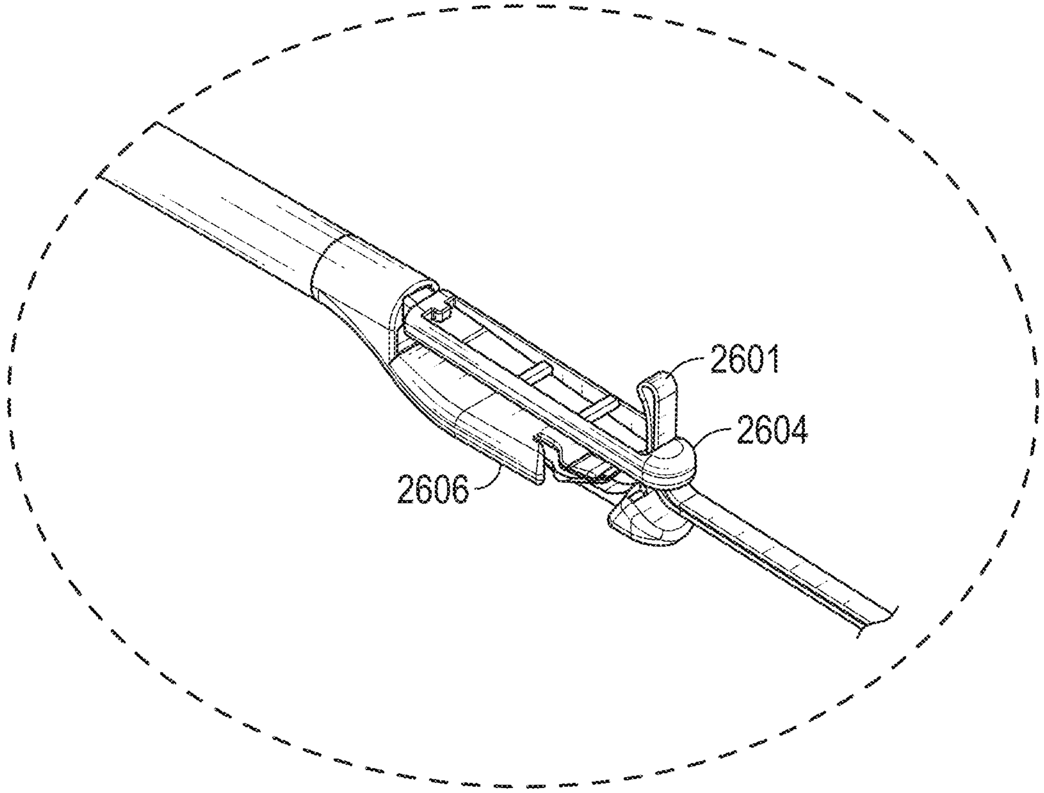

FIGS. 33A-33B illustrate the jaws 2604, 2606 in a closed configuration with the needle 2612 in an undeployed configuration. The suture retainer 2622 can keep the suture 2601 in position (e.g., forming a loop and extending through the upper jaw member 2604) as the needle 2612 is retracted from a deployed configuration to an undeployed configuration (e.g., retracted back into the lower jaw member 2606). To unload the suture 2601, a user can pull up on the suture loop that is maintained across the tissue by the suture retainer 2622.

Figure 34:
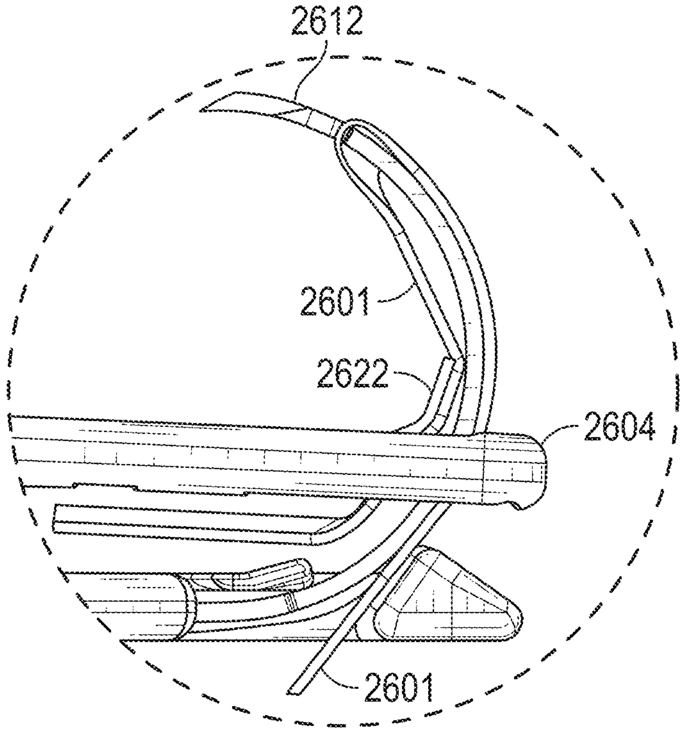
FIG. 34 shows a side view of the needle in a deployed configuration.

FIG. 34 illustrates a side view of the needle 2612 in a deployed configuration. The suture 2601 can be retained on a portion of the needle 2612 proximal to the distal end. For example, the suture 2601 can be retained on a notch of the needle. In some embodiments, the needle 2612 can include a hook, clip, groove, slot, or other mechanism for retaining the suture 2601.

Figure 35:
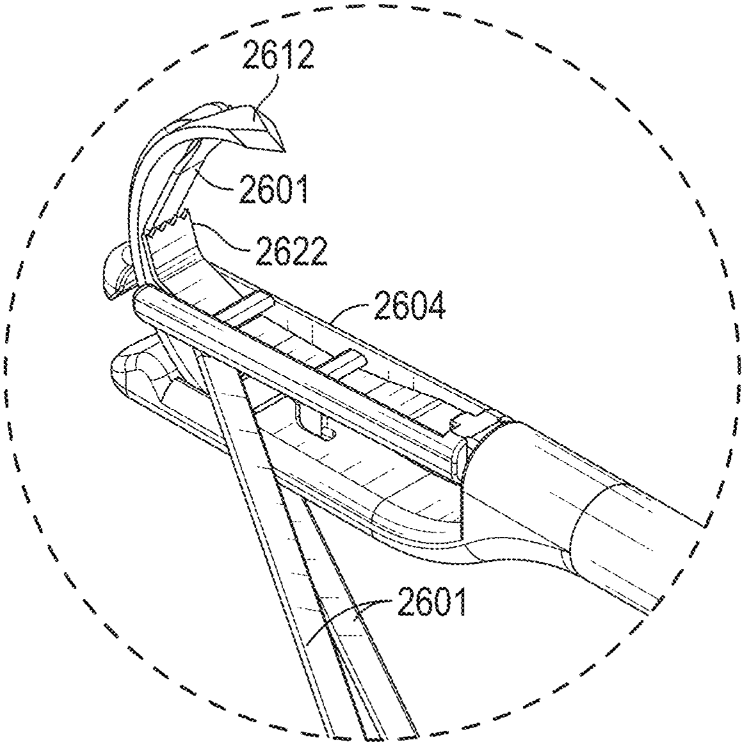
FIG. 35 shows the distal end of a suture passer with the jaws in a closed configuration and the needle in a deployed configuration.
Figure 36:
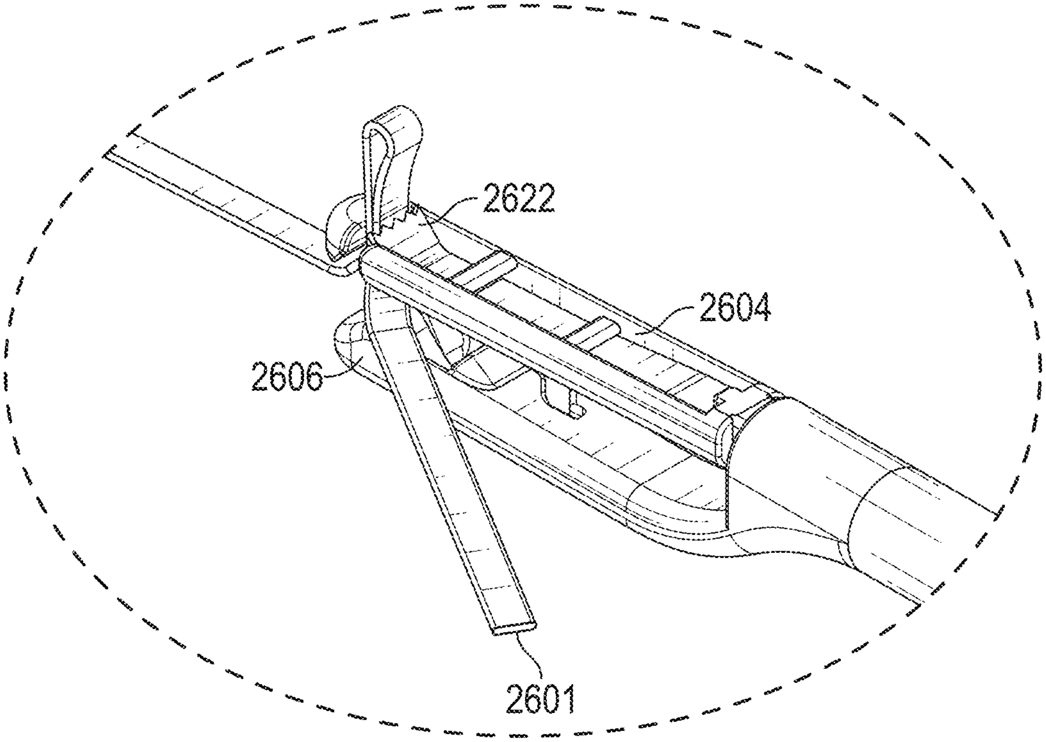
FIG. 36 shows a distal end of the suture passer when the needle retracts from a deployed configuration to a undeployed configuration.
Figure 37:
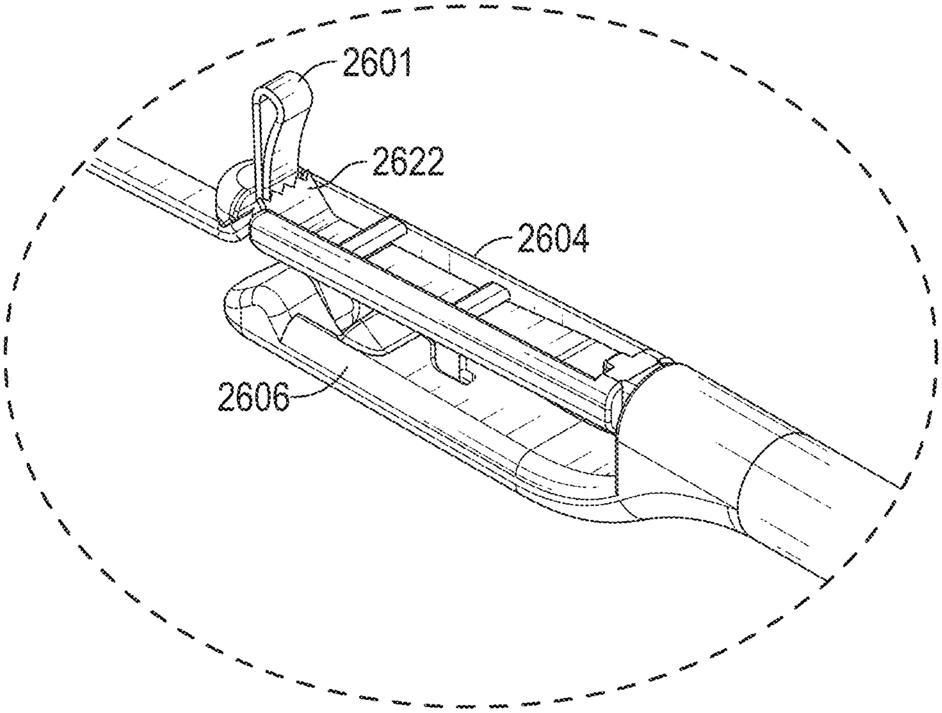
FIG. 37 shows a distal end of a suture passer in a closed jaws configuration and needle undeployed configuration.

FIGS. 35-37 illustrates a perspective view of a suture 2601 being loaded into a suture passer (e.g., any of the suture passer embodiments disclosed herein).

FIG. 35 illustrates the distal end of a suture passer (e.g., suture passer 100, 500, 600, 700, 2100) with the jaws 2604, 2606 in a closed configuration and the needle 2612 in a deployed configuration. In the deployed configuration, the needle 2612 can extend from the lower jaw member 2606 past the upper jaw member 2604. The suture retainer 2622 can be positioned on or near the upper jaw member 2604. When the needle 2612 moves from an undeployed configuration to a deployed configuration, the needle 2612 can move such that the suture retainer 2622 grips the suture 2601. For example, the suture retainer 2622 can be biased towards a portion of the upper jaw member 2604 such that the suture 2601 can be gripped between the suture retainer 2622 and the portion of the upper jaw member 2604 when the needle 2612 moves the suture 2601 through (e.g., between) the suture retainer 2622 and the portion of the upper jaw member 2604. In some embodiments, the suture retainer 2622 can grip the suture 2601 between the suture retainer 2622 and the lower jaw member 2606, or between two portions of the suture retainer 2622.

FIG. 36 illustrates the distal end of the suture passer when the needle 2612 retracts from the deployed configuration the undeployed configuration. The suture 2601 can be gripped by the suture retainer 2622 such that the suture extends or protrudes through or beyond the upper jaw member 2604. For example, a loop of suture 2601 can extend through the upper jaw member 2604. To unload the suture, the user can pull up on the suture loop that is maintained across the tissue by the suture retainer 2622. In some embodiments, the suture 2601 can be released from the upper jaw member 2604 by pulling up on a short suture end, which may prevent damage, such as fraying, to the suture that could otherwise occur during intricate unloading of the suture. The upper jaw member 2604 can include an opening or a slot in the side of the upper jaw, proximal to an area where the suture retainer 2622 grabs the suture 2601, through which the end of the suture 2601 can be pulled to unload the suture 2601.

FIG. 37 illustrates the distal end of the suture passer when the needle 2612 is retracted (e.g., an undeployed configuration), the jaws 2604, 2606 are closed (e.g., closed jaws configuration), and the suture 2601 is retained by the suture retainer 2622 (e.g., suture retained configuration). The suture 2601 can be retained in a loop through the upper jaw 2604. The suture 2601 can be retained (e.g., grabbed, pinched, held, etc.) such that a user can move the suture 2601 by moving the upper jaw 2604 (e.g., by moving the handle) after the suture 2601 has been passed through tissue by the needle 2612.

EXAMPLES

Example 1. A system for passing a suture comprising: a handle comprising a trigger; an elongate member extending from the handle; a first jaw member extending from a distal end of the elongate member and configured for angular movement relative to the elongate member; and a second jaw member extending from the distal end of the elongate member, the second jaw member comprising: a curved portion extending from the distal end of the elongate member and curved away from the first jaw member; a straight portion extending from a distal end of the curved portion; and a tissue penetrator positioned on the straight portion of the second jaw member, the tissue penetrator configured to shift between a retracted position and an engaged position, the tissue penetrator configured to be parallel with the straight portion of the second jaw member in the retracted position, and the tissue penetrator configured to extend through the first jaw member in the engaged position, wherein the trigger is configured to shift the tissue penetrator between the retracted position and the engaged position.

Example 2. The system of example 1, wherein the tissue penetrator is a needle.

Example 3. The system of example 2, wherein a distal end of the needle is curved toward the second jaw member in the engaged position.

Example 4. The system of any one of examples 1-3, wherein the second jaw member comprises a shoulder configured to direct the tissue penetrator toward the first jaw member.

Example 5. The system of any one of examples 1-4, further comprising a suture loader in the second jaw member.

Example 6. The system of example 5, wherein the suture loader comprises a notch in the straight portion of the second jaw member.

Example 7. The system of example 6, wherein the suture loader comprises a slot perpendicular to the notch and aligned with the tissue penetrator.

Example 8. A method for passing a suture, the method comprising: providing a suture passer comprising: an elongate member; a first jaw member extending from a distal end of the elongate member; and a second jaw member extending from the distal end of the elongate member, the second jaw member comprising: a curved portion extending from the distal end of the elongate member and curved away from the first jaw member; a straight portion extending from a distal end of the curved portion; and routing a suture in a suture loader in the second jaw member such that the suture contacts a tissue penetrator; positioning the first jaw member and the second jaw member around a tissue; moving the first jaw member toward the second jaw member to engage the tissue; and deploying the tissue penetrator from the second jaw member through the tissue and through the first jaw member.

Example 9. The method of example 8, further comprising retracting the tissue penetrator in the second jaw member.

Example 10. The method of any one of examples 8 or 9, further comprising moving the first jaw member away from the second jaw member.

Example 11. The method of any one of examples 8-10, wherein deploying the tissue penetrator comprises abutting, with the tissue penetrator, a shoulder of the second jaw member.

Example 12. The method of any one of examples 8-11, wherein moving the first jaw member toward the second jaw member comprises actuating a trigger to move the first jaw member toward the second jaw member.

Example 13. The method of any one of examples 8-12, wherein deploying the tissue penetrator from the second jaw member comprises actuating a trigger to deploy the tissue penetrator from the second jaw member.

Example 14. A system for passing a suture comprising: a handle comprising a trigger; an elongate member extending from the handle; a first jaw member extending from a distal end of the elongate member and configured for angular movement relative to the elongate member; and a second jaw member extending from the distal end of the elongate member, the second jaw member comprising a tissue penetrator, the tissue penetrator configured to shift between a retracted position and an engaged position, the tissue penetrator configured to be parallel with the second jaw member in the retracted position, and the tissue penetrator configured to extend through the first jaw member in the engaged position, wherein the tissue penetrator comprises a downward curved distal end in the engaged position, and wherein the trigger is configured to shift the tissue penetrator between the retracted position and the engaged position.

Example 15. The system of example 14, wherein the tissue penetrator is a needle.

Example 16. The system of any one of examples 14 or 15, wherein the second jaw member comprises a shoulder configured to direct the tissue penetrator toward the first jaw member.

Example 17. The system of any one of examples 14-16, further comprising a suture loader in the second jaw member.

Example 18. The system of example 17, wherein the suture loader comprises a notch in the second jaw member.

Example 19. The system of example 18, wherein the suture loader comprises a slot perpendicular to the notch and aligned with the tissue penetrator.

Example 20. A kit comprising: a suture passer comprising: a handle comprising a trigger; an elongate member extending from the handle; a first jaw member extending from a distal end of the elongate member and configured for angular movement relative to the elongate member; and a second jaw member extending from the distal end of the elongate member, the second jaw member comprising: a curved portion extending from the distal end of the elongate member and curved away from the first jaw member; a straight portion extending from a distal end of the curved portion; and a tissue penetrator positioned on the straight portion of the second jaw member, the tissue penetrator configured to shift between a retracted position and an engaged position, the tissue penetrator configured to be parallel with the straight portion in the retracted position, and the tissue penetrator configured to extend through the first jaw member in the engaged position, wherein the trigger is configured to shift the tissue penetrator between the retracted position and the engaged position; and a suture.

Example 21. A method of loading a suture comprising: providing a suture passer comprising: an elongate member; a first jaw member extending from a distal end of the elongate member; a second jaw member extending from the distal end of the elongate member, the second jaw member comprising: a curved portion extending from the distal end of the elongate member and curved away from the first jaw member; a straight portion extending from a distal end of the curved portion, the straight portion include a suture loader; a tissue penetrator configured to extend from the second jaw member and through the first jaw member, the tissue penetrator comprising a notch on a side of the tissue penetrator; and a suture retainer configured to retain the suture; positioning a suture loop over the second jaw member and within the suture loader; moving the first jaw member toward the second jaw member; deploying the tissue penetrator from the second jaw member and through the first jaw member, wherein the notch of the tissue penetrator captures the suture loop, the tissue penetrator moves the suture loop through the first jaw member, and the suture retainer retains the suture loop through the first jaw member.

Example 22. The method of example 21, further comprising retracting the tissue penetrator in the second jaw member.

Example 23. The method of any one of examples 21-22, further comprising moving the first jaw member away from the second jaw member.

Example 24. The method of any one of examples 21-23, wherein moving the first jaw member toward the second jaw member comprises actuating a trigger to move the first jaw member toward the second jaw member.

Example 25. The method of any one of examples 21-24, wherein deploying the tissue penetrator from the second jaw member comprises actuating a trigger to deploy the tissue penetrator from the second jaw member.

Example 26. The method of any one of examples 21-25, wherein moving the first jaw member toward the second jaw member comprises partially actuating a trigger to move the first jaw member toward the second jaw member, and deploying the tissue penetrator from the second jaw member comprises fully actuating the trigger to deploy the tissue penetrator from the second jaw member.

Example 27. The method of any one of examples 21-26, further comprising unloading the suture loop by pulling the suture loop retained by the suture retainer.

Example 28. The method of any one of examples 21-27, further comprising unloading the suture loop by pulling on an end of the suture loop.

Example 29. The method of any one of examples 21-28, wherein unloading the suture loop further comprises pulling the end of the suture loop through an opening in a side of the second jaw member.

Example 30. The method of any one of examples 21-29, wherein the suture retainer retains the suture by pressing the suture against a portion of the second jaw member.

Example 31. The method of any one of examples 21-30, wherein the tissue penetrator is a needle.

Example 32. The method of any one of examples 21-31, wherein deploying the tissue penetrator comprises deploying the tissue penetrator such that the tissue penetrator curves downwards towards the second jaw member.

Example 33. The method of any one of examples 21-32, wherein the second jaw member comprises a shoulder configured to direct the tissue penetrator toward the first jaw member.

Example 34. The method of any one of examples 21-33, wherein the suture loader comprises a notch in the straight portion of the second jaw member.

Example 35. The method of example 34, wherein the suture loader comprises a slot perpendicular to the notch and aligned with the tissue penetrator.

Other Variations

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

Conditional language used herein, such as, among others, “can,” “could”, “might,” “may,” “e.g.,” and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Headings are included herein for reference and to aid in locating various sections. These headings are not intended to limit the scope of the concepts described with respect thereto. Such concepts may have applicability throughout the entire specification.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A system for passing a suture comprising:

a handle comprising a trigger;

an elongate member extending from the handle;

a first jaw member extending from a distal end of the elongate member and configured for angular movement relative to the elongate member; and a second jaw member extending from the distal end of the elongate member, the second jaw member comprising:

a curved portion extending from the distal end of the elongate member and curved away from the first jaw member;

a straight portion extending from a distal end of the curved portion; wherein the curved portion is configured to offset from the straight portion with respect to the elongate member; and a tissue penetrator positioned on the straight portion of the second jaw member, the tissue penetrator configured to shift between a retracted position and an engaged position, the tissue penetrator configured to be parallel with the straight portion of the second jaw member in the retracted position, and the tissue penetrator configured to extend through the first jaw member in the engaged position, wherein the trigger is configured to shift the tissue penetrator between the retracted position and the engaged position.

2. The system of claim 1, wherein the tissue penetrator is a needle.

3. The system of claim 2, wherein a distal end of the needle is curved toward the second jaw member in the engaged position.

4. The system of claim 1, wherein the second jaw member comprises a shoulder configured to direct the tissue penetrator toward the first jaw member.

5. The system of claim 1, further comprising a suture loader in the second jaw member.

6. The system of claim 5, wherein the suture loader comprises a notch in the straight portion of the second jaw member.

7. The system of claim 6, wherein the suture loader comprises a slot perpendicular to the notch and aligned with the tissue penetrator.

8. The system of claim 1, further comprising a notch in the tissue penetrator and a suture retainer, wherein the notch of the tissue penetrator is configured to capture a suture loop, the tissue penetrator is configured to move the suture loop through the first jaw member, and the suture retainer is configured to retain the suture loop.

9. The system of claim 8, further comprising the suture loop, the suture loop configured to be released from the suture retainer by pulling on an end of the suture loop.

10. The system of claim 8, wherein the notch of the tissue penetrator is proximal to a distal end of the tissue penetrator.

11. A suture passer device comprising:

an elongate member configured to be coupled with a handle comprising a trigger;

a first jaw member extending from a distal end of the elongate member and configured for angular movement relative to the elongate member; and a second jaw member extending from the distal end of the elongate member, the second jaw member comprising:

a curved portion extending from the distal end of the elongate member and curved away from the first jaw member;

a straight portion extending from a distal end of the curved portion; wherein the curved portion is configured to offset from the straight portion with respect to the elongate member; and a tissue penetrator positioned on the straight portion of the second jaw member, the tissue penetrator configured to shift between a retracted position and an engaged position, the tissue penetrator configured to be parallel with the straight portion of the second jaw member in the retracted position, and the tissue penetrator configured to extend through the first jaw member in the engaged position, wherein the tissue penetrator is configured to shift between the retracted position and the engaged position by actuating the trigger when the handle and the elongate member are coupled.

12. The device of claim 11, wherein the tissue penetrator is a needle.

13. The device of claim 12, wherein a distal end of the needle is curved toward the second jaw member in the engaged position.

14. The device of claim 11, wherein the second jaw member comprises a shoulder configured to direct the tissue penetrator toward the first jaw member.

15. The device of claim 11, further comprising a suture loader in the second jaw member.

16. The device of claim 15, wherein the suture loader comprises a notch in the straight portion of the second jaw member.

17. The device of claim 16, wherein the suture loader comprises a slot perpendicular to the notch and aligned with the tissue penetrator.

18. The device of claim 11, further comprising a notch in the tissue penetrator and a suture retainer, wherein the notch of the tissue penetrator is configured to capture a suture loop, the tissue penetrator is configured to move the suture loop through the first jaw member, and the suture retainer is configured to retain the suture loop.

19. The device of claim 18, further comprising the suture loop, the suture loop configured to be released from the suture retainer by pulling on an end of the suture loop.

20. The device of claim 18, wherein the notch of the tissue penetrator is proximal to a distal end of the tissue penetrator.

* * * * *